United States Patent
Lee et al.

(10) Patent No.: US 8,314,123 B2
(45) Date of Patent: *Nov. 20, 2012

(54) 5, 6, OR 7-SUBSTITUTED-3-(HETERO) ARYLISOQUINOLINAMINE DERIVATIVES AND THERAPEUTIC USE THEREOF

(75) Inventors: Young Bok Lee, Clarksville, MD (US); Chang Ho Ahn, Potomac, MD (US); Won-Jea Cho, Kwangju (KR)

(73) Assignee: Rexahn Pharmaceuticals, Inc., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/268,678

(22) Filed: Oct. 7, 2011

(65) Prior Publication Data

US 2012/0029012 A1 Feb. 2, 2012

Related U.S. Application Data

(63) Continuation of application No. 11/984,288, filed on Nov. 15, 2007, now Pat. No. 8,034,829.

(60) Provisional application No. 60/866,269, filed on Nov. 17, 2006.

(51) Int. Cl.
*A61K 31/472* (2006.01)
*C07D 217/22* (2006.01)

(52) U.S. Cl. ........................ 514/310; 546/143

(58) Field of Classification Search ........................ None
See application file for complete search history.

(56) References Cited

U.S. PATENT DOCUMENTS

| 4,942,163 A | 7/1990 | Behrens |
| 8,034,829 B2 * | 10/2011 | Lee et al. ...................... 514/310 |
| 2007/0185160 A1 | 8/2007 | Hattori et al. |

FOREIGN PATENT DOCUMENTS

| DE | 22 43 789 A1 | 3/1973 |
| KR | 2002 0074568 A | 10/2002 |
| KR | 0412319 | 12/2003 |
| WO | WO-2005/075431 | 8/2005 |
| WO | WO-2005/075432 | 8/2005 |

OTHER PUBLICATIONS

Cho et al., "Molecular Modeling of 3-Arylisoquinoline Antitumor Agents Active Against A-549. A Comparative Molecular Field Analysis Study," Bioorganic & Medicinal Chemistry vol. 10, pp. 2953-2961, 2002.
Kaiser et al., "Facile Synthesis of 1-Amino-3-arylisoquinolines," Synthesis, No. 11, pp. 805-806, 1974.
Pijper et al., "Synthesis and antimycoplasmal activity of 2,2'-bipyridyl analogs, Part I. 1-Amino-3-(2-pyridyl) isoquinolines," European Journal of Medicinal Chemistry, vol. 19, No. 5, pp. 389-392, 1984.
Van Der Goot et al., "The growth-inhibitory action of some 1-aminoisoquinolines and related compounds on *Mycoplasma gallisepticum*" European Journal of Medicinal Chemistry, vol. 10, No. 6, pp. 603-606, 1975.
Van Der Goot et al., "A new synthesis of 1-aminoisoquinolines," Chimica Therapeutica, vol. 7, No. 3, pp. 185-188, 1972.
Cho et al., "Synthesis of New 3-Arylisoquinolinolinamines: Effect on Topoisomerase I Inhibition and Cytotoxicity," Bioorganic & Medicinal Chemistry Letters, vol. 13, No. 24, pp. 4451-4454, 2003.
Bordner et al., "1,3-Diamino-6,7-dimethoxyisoquinoline Derivatives as Potential $\alpha_1$-Adrenoceptor Antagonists", Journal of Medicinal Chemistry, vol. 31, No. 5, pp. 1036-1039, 1988.

* cited by examiner

*Primary Examiner* — Zinna Northington Davis
(74) *Attorney, Agent, or Firm* — Venable LLP; Keith G. Haddaway; Lars H. Genieser

(57) ABSTRACT

The present invention relates to 5, 6, or 7-substituted-3-(hetero)arylisoquinolinamine derivatives represented by general formula D, their pharmacologically acceptable salts thereof, and compositions containing such compounds. Methods for treating hyperproliferative disorders by administering the compounds are also included.

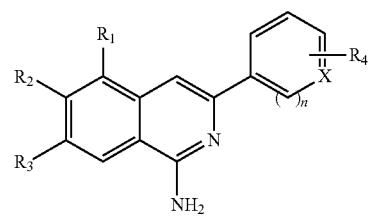

16 Claims, No Drawings

US 8,314,123 B2

5, 6, OR 7-SUBSTITUTED-3-(HETERO) ARYLISOQUINOLINAMINE DERIVATIVES AND THERAPEUTIC USE THEREOF

CROSS REFERENCE TO RELATED APPLICATION

This application is a Continuation of U.S. application Ser. No. 11/984,288 filed Nov. 15, 2007, now U.S. Pat. No. 8,034,829, which claims priority to U.S. Provisional Application No. 60/866,269 filed Nov. 17, 2006, the contents of each of which are hereby incorporated by reference in their entirety.

FIELD OF THE INVENTION

The present invention relates to novel 5, 6, or 7-substituted-3-(hetero)aryl-isoquinolinamine compounds, their pharmacologically acceptable salts thereof, and compositions containing such compounds and their therapeutic methods for the treatment of hyperproliferative disorders, including cancers, by administering 5, 6, or 7-substituted-3-(hetero)aryl-isoquinolinamine compounds.

BACKGROUND OF THE INVENTION

Chemotherapeutics kill tumor cells by interfering with various stages of the cell division process. There are a number of classes of chemotherapeutics including alkylating agents (e.g., cyclophosphamide, carmustine, cisplatin), antimetabolites (e.g., methotrexate, 5-FU, gemcitabine), cytotoxic antibiotics (e.g., doxorubicin, mitomycin) and plant derivatives (e.g., paclitaxel, vincristine, etoposide). Chemotherapy is used as a primary treatment for leukemias, other blood cancers, and inoperable or metastatic solid cancers.

Current chemotherapeutic agents suffer several problems, including limited efficacy, debilitating adverse side effects and development of multidrug resistance.

SUMMARY OF THE INVENTION

A series of 5, 6, or 7-substituted-3-(hetero)arylisoquinolinamine compounds were synthesized and analyzed for therapeutic activities, including anti-cancer activities. 5, 6, or 7-Substituted-3-(hetero)arylisoquinolinamine compounds of the invention are demonstrated as useful for the treatment of hyperproliferative disorders, including tumors, such as prostate tumors, colon tumors, pancreatic tumors, and ovarian tumors.

The present invention is directed to novel 5, 6, or 7-substituted-3-(hetero)aryl-isoquinolinamine compounds and derivatives. The present invention is also directed to the use of 5, 6, or 7-substituted-3-(hetero)arylisoquinolinamine derivatives as antitumor agent.

DETAILED DESCRIPTION OF THE INVENTION

The terms "5, 6, or 7-substituted-3-(hetero)arylisoquinolinamine", "5, 6, or 7-substituted-3-(hetero)arylisoquinolinamine compound", and "5, 6, or 7-substituted-3-(hetero) arylisoquinolinamine derivative" are used interchangeably in this application to mean compounds of formula D, as defined below. All scientific and technical terms used in this application have meanings commonly used in the art unless otherwise specified. As used in this application, the following words or phrases have the meanings specified.

As used herein, "pharmaceutically acceptable carrier" means any solid or liquid material which, when combined with a compound of the invention, allows the compound to retain biological activity, such as the ability to potentiate antibacterial activity of mast cells and macrophages. Examples include, but are not limited to, any of the standard pharmaceutical carriers such as a phosphate buffered saline solution, water, emulsions such as oil/water emulsions, and various types of wetting agents. Compositions comprising such carriers are formulated by well-known conventional methods (see, for example, Remington's Pharmaceutical Sciences, Chapter 43, 14th Ed., Mack Publishing Co., Easton, Pa.).

The term "conjugate" means a compound formed as a composite between two or more molecules. More specifically, in the present invention, the 5, 6, or 7-substituted-3-(hetero)arylisoquinolinamine derivative can be bonded, for example, covalently bonded, to cell-specific targeting moieties forming a conjugate compound for efficient and specific delivery of the agent to a cell of interest.

The phrase "targeting moiety" means a molecule which serves to deliver the compound of the invention to a specific site for the desired activity. Targeting moieties include, for example, molecules that specifically bind molecules on a specific cell surface. Such targeting moieties useful in the invention include anti-cell surface antigen antibodies. Cytokines, including interleukins and factors such as granulocyte/macrophage stimulating factor (GMCSF) are also specific targeting moieties, known to bind to specific cells expressing high levels of their receptors.

The term "prodrug moiety" is a substituent group which facilitates use of a compound of the invention, for example by facilitating entry of the drug into cells or administration of the compound. The prodrug moiety may be cleaved from the compound, for example by cleavage enzymes in vivo. Examples of prodrug moieties include phosphate groups, peptide linkers, and sugars, which moieties can be hydrolyzed in vivo.

The term "hyperproliferative disorder" refers to disorders characterized by an abnormal or pathological proliferation of cells, for example, tumors, cancers, neoplastic tissue and other premalignant and non-neoplastic or non-malignant hyperproliferative disorders.

Examples of tumors, cancers, and neoplastic tissue that can be treated by the present invention include but are not limited to malignant disorders such as breast cancers; osteosarcomas; angiosarcomas; fibrosarcomas and other sarcomas; leukemias; lymphomas; sinus tumors; ovarian, urethral, bladder, prostate and other genitourinary cancers; colon esophageal and stomach cancers and other gastrointestinal cancers; lung cancers; myelomas; pancreatic cancers; liver cancers; kidney cancers; endocrine cancers; skin cancers; and brain or central and peripheral nervous (CNS) system tumors, malignant or benign, including gliomas and neuroblastomas.

Examples of premalignant and non-neoplastic or non-malignant hyperproliferative disorders include but are not limited to myelodysplastic disorders; cervical carcinoma-in-situ; familial intestinal polyposes such as Gardner syndrome; oral leukoplakias; histiocytoses; keloids; hemangiomas; hyperproliferative arterial stenosis, inflammatory arthritis; hyperkeratoses and papulosquamous eruptions including arthritis. Also included are viral induced hyperproliferative diseases such as warts and EBV induced disease (i.e., infectious mononucleosis), scar formation, and the like. The methods of treatment disclosed herein may be employed with any subject known or suspected of carrying or at risk of developing a hyperproliferative disorder as defined herein.

As used herein, "treatment" of a hyperproliferative disorder refers to methods of killing, inhibiting or slowing the growth or increase in size of a body or population of hyperproliferative cells or tumor or cancerous growth, reducing hyperproliferative cell numbers, or preventing spread to other anatomic sites, as well as reducing the size of a hyperproliferative growth or numbers of hyperproliferative cells. As used herein, "treatment" is not necessarily meant to imply cure or complete abolition of hyperproliferative growths. As used herein, a treatment effective amount is an amount effective to result in the killing, the slowing of the rate of growth of hyperproliferative cells, the decrease in size of a body of hyperproliferative cells, and/or the reduction in number of hyperproliferative cells. The potentiating agent (or agents) is included in an amount sufficient to enhance the activity of the first compound, such that the two (or more) compounds together have greater therapeutic efficacy than the individual compounds given alone (e.g., due to synergistic interaction; reduced combined toxicity, etc.).

Novel 5, 6, or 7-substituted-3-(hetero)arylisoquinolinamine compounds may provide potent new therapeutic molecules for the treatment of disorders such as tumors. In association with new development of an anti-tumor agent, Korea Patent No. 0412319 discloses the 3-arylisoquinolinamine compounds having formula (A) wherein $R_6$ is hydrogen or 6-methyl, $R_7$ is hydrogen, mono 2- or 3- or 4-methyl, and $R_8$ is amine or benzylamine or 4-methoxybenzylamine or piperidine or trimethylethanediamine or morpholine or 4-methylpiperazine or 4-methylhomopiperazine. Among compounds disclosed in Korea Patent No. 0412319, 6-methyl-3-(2-methylphenyl)-1-isoquinolinamine was claimed as an anticancer agent having significant therapeutic activity against human A549 lung carcinoma, human HCT-15 colon adenocarcinoma, human SK-OV-3 ovarian adenocarcinoma and human SK-MEL-2 melanoma.

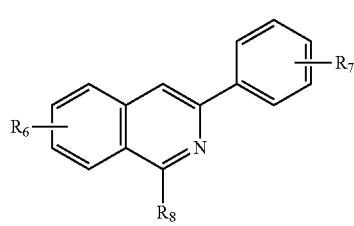

(A)

U.S. Pat. No. 4,942,163 issued to Carl H. Behrens et al. on Jul. 17, 1990, discloses 3-(1-naphthalenyl)-1(2H) isoquinolinones and 3-(1-naphthalenyl)-1-isoquinolineamines of the formula (B) as useful cancer chemotherapeutic agents.

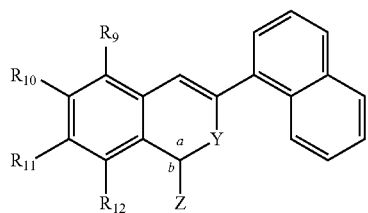

(B)

Furthermore, in PCT International Application Nos. WO 2005/075431 and WO 2005/075432, the preparation of 1-(2H)-isoquinolone derivatives having formula (C) is presented.

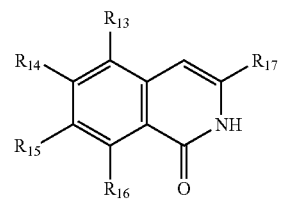

(C)

The present invention is directed to 5, 6, or 7-substituted-3-(hetero)arylisoquinolinamine derivatives with prominent antitumor activities, very low toxicities and good solubility in water and presents novel 5, 6, or 7-substituted-3-(hetero)arylisoquinolinamine derivatives which are not claimed in Korea Patent No. 0412319 and U.S. Pat. No. 4,942,163 and the process of preparation and strong antitumor activities of these new compounds.

More particularly, the present invention is directed to 5, 6, or 7-substituted-3-(hetero)arylisoquinolinamine compounds and their use in the treatment of a hyperproliferative disorder, disease or condition in a subject (e.g., a human patient or other animal subject). Methods according to the invention comprise administering to a subject an effective amount of a 5, 6, or 7-substituted-3-(hetero)arylisoquinolinamine compound according to the invention. Such a treatment can, e.g., prevent, ameliorate, and/or inhibit symptoms of the hyperproliferative condition, and/or can prevent or inhibit cellular proliferation or growth, for instance in a tumor, such as a malignant neoplasm. A treatment strategy of the invention would decrease the tumor burden, at least to a measurable degree, and improve survival of patients suffering from the hyperproliferative condition. Among the diseases, disorders and conditions susceptible to treatment by agents of the invention are neoplasms, and more specifically tumors of various origins (lung, colon, stomach, smooth muscle, esophagus, non-Hodgkin's lymphoma, non-small cell lung cancer, etc.).

Compounds useful in methods of the invention include 5, 6, or 7-substituted-3-(hetero)arylisoquinolinamines having the formula D:

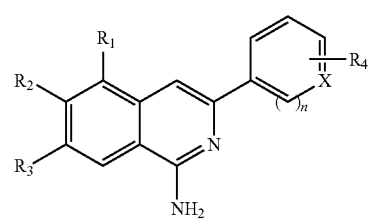

D wherein
n is 0 or 1;
X is independently N, C, O or S;
$R_1$, $R_2$, and $R_3$ are independently H, halogen, $NH_2$, $NHR_5$, $N(R_5)_2$, —O—$R_5$ or $R_5$ optionally substituted with —O$R_5$;
$R_4$ is one or two substituents selected from H, 3,4-methylendioxide, halogen, —O—$R_5$ or $R_5$ optionally substituted with —O—$R_5$; and
$R_5$ is $C_1$-$C_6$ alkyl. Where the compound includes more than one group $R_5$, each of the $R_5$ groups may be the same or different.
In the above definitions, the designation "halogen" represents F, Cl, Br or I.

As used herein, $C_1$-$C_6$ alkyl represents linear, branched and cyclic alkyl groups having from 1 to 6 Carbon atoms including methyl, ethyl, propyl, isopropyl, n-butyl, isobutyl, t-butyl, n-pentyl, isopentyl, n-hexyl, isohexyl and cyclohexyl.

Specifically excluded from the scope of the present invention are compounds having (a) $R_1$=$R_2$=$R_3$=H, n=1, X=C and $R_4$=H, 2-methyl, 3-methyl or 4-methyl and (b) compounds having $R_1$=$R_3$=H, $R_2$=methyl, n=1, X=C and $R_4$=H, 2-methyl or 3-methyl.

The present invention also includes pharmaceutically acceptable salts of these compounds. Pharmaceutically acceptable salts of compounds of the general formula (D) are pharmaceutically acceptable inorganic, organic acids, alkali metal and ammonium; for example, salts with inorganic acids such as hydrochloric acid, bromic acid, sulfuric acid, sodium hydrogensulfate, phosphoric acid, nitric acid, carbonic acid; salts with organic acids such as formic acid, acetic acid, propionic acid, oxalic acid, succinic acid, benzoic acid, citric acid, maleic acid, malonic acid, tartaric acid, gluconic acid, lactic acid, fumaric acid, lactobionic acid, salicylic acid, acetyl salicylic acid(aspirin); salts with amino acids such as glycine, alanine, valine, leucine, isoleucine, serine, cysteine, cystine, asparaginic acid, glutamic acid, lysine, arginine, tyrosine, proline; salts with sulfonic acids such as methane sulfonic acid, ethane sulfonic acid, benzene sulfonic acid, toluene sulfonic acid; an alkali metal salt, for example, a sodium or potassium salt; an alkali earth metal salt, for example, a calcium or magnesium salt; an ammonium salt; a salt with an organic base which affords a physiologically-acceptable, for example a salt with methylamine, dimethylamine, trimethylamine, piperidine, morpholine or tris-(2-hydroxyethyl)amine, or the like.

Compounds of the present invention can be very active against a wide range of hyperproliferative diseases, including tumors, and used as an anti-tumor agent. For example, compounds according to the invention can be active against tumors of the ovary, tumors of the prostate, breast tumors, kidney tumors, colon tumors, pancreatic tumors, brain tumors and melanoma. By very active, it is meant that a compound can have an $IC_{50}$ of 5.0 µM or less, 2.0 or less, 1.0 µM or less, 0.5 µM or less, 0.2 µM or less, or 0.1 µM or less with respect to at least one cell line for a particular tumor.

The novel compounds of the general formula (D) and pharmaceutically acceptable salts thereof may be combined with a non-toxic pharmaceutically acceptable vehicle such as a carrier, adjuvant, and/or excipient and then the mixture may be administered orally or parenterally in the form of tablets, capsules, troches, solutions, suspensions to prevent or treat various kinds of tumors of human beings or mammals.

Vehicles which can be used in the preparation of pharmaceutical compositions containing the compound of the general formula (D) as the active ingredient may include a sweetening agent, a binding agent, a dissolving agent, aids for dissolution, a wetting agent, an emulsifying agent, an isotonic agent, an adsorbent, a degrading agent, an antioxidant, an antiseptics, a lubricating agent, a filler, perfume or the like; such as lactose, dextrose, sucrose, mannitol, sorbitol, cellulose, glycine, silica, talc, stearic acid, stearin, magnesium stearate, calcium stearate, magnesium aluminum silicate, starch, gelatin, tragacanth gum, glycine, silica, alginic acid, sodium alginate, methyl cellulose, sodium carboxy methyl cellulose, agar, water, ethanol, polyethylene glycol, polyvinyl pyrrolidone, sodium chloride, potassium chloride, orange essence, strawberry essence, vanilla aroma or the like.

The 5, 6, or 7-substituted-3-(hetero)arylisoquinolinamine compounds of the invention can be formulated as pharmaceutical compositions and administered to a subject in need of treatment, for example a mammal, such as a human patient, in a variety of forms adapted to the chosen route of administration, for example, orally or parenterally, by intravenous, intramuscular, topical or subcutaneous routes, or direct injection into the hyperproliferative tissue or cells.

Thus, 5, 6, or 7-substituted-3-(hetero)arylisoquinolinamine compounds of the invention may be systemically administered, e.g., orally, in combination with a pharmaceutically acceptable vehicle such as an inert diluent or an assimilable edible carrier, or by inhalation or insufflation. They may be enclosed in hard or soft shell gelatin capsules, may be compressed into tablets, or may be incorporated directly with the food of the patient's diet. For oral therapeutic administration, the 5, 6, or 7-substituted-3-(hetero)arylisoquinolinamine compounds may be combined with one or more excipients and used in the form of ingestible tablets, buccal tablets, troches, capsules, elixirs, suspensions, syrups, wafers, and the like. The 5, 6, or 7-substituted-3-(hetero)arylisoquinolinamine compounds may be combined with a fine inert powdered carrier and inhaled by the subject or insufflated. Such compositions and preparations should contain at least 0.1% 5, 6, or 7-substituted-3-(hetero)arylisoquinolinamine compounds. The percentage of the compositions and preparations may, of course, be varied and may conveniently be between about 2% to about 60% of the weight of a given unit dosage form. The amount of 5, 6, or 7-substituted-3-(hetero)arylisoquinolinamine compounds in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the 5, 6, or 7-substituted-3-(hetero)arylisoquinolinamine compounds may be incorporated into sustained-release preparations and devices.

The 5, 6, or 7-substituted-3-(hetero)arylisoquinolinamine compounds may also be administered intravenously or intraperitoneally by infusion or injection. Solutions of the 5, 6, or 7-substituted-3-(hetero)arylisoquinolinamine compounds can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the 5, 6, or 7-substituted-3-(hetero)arylisoquinolinamine compounds which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the 5, 6, or 7-substituted-3-(hetero)arylisoquinolinamine compounds in the required amount in the appropriate solvent with various of the other ingredients enumerated above, as required, followed by filter sterilization. In the case of sterile powders for the preparation of sterile injectable solutions, the preferred methods of preparation are vacuum drying and freeze drying techniques, which yield a powder of the active ingredient plus any additional desired ingredient present in the previously sterile-filtered solutions.

For topical administration, the 5, 6, or 7-substituted-3-(hetero)arylisoquinolinamine compounds may be applied in pure form. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Other solid carriers include nontoxic polymeric nanoparticles or microparticles. Useful liquid carriers include water, alcohols or glycols or water/alcohol/glycol blends, in which the 5, 6, or 7-substituted-3-(hetero)arylisoquinolinamine compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the 5, 6, or 7-substituted-3-(hetero)arylisoquinolinamine compounds to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of 5, 6, or 7-substituted-3-(hetero)arylisoquinolinamine compounds can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the 5, 6, or 7-substituted-3-(hetero)arylisoquinolinamine compounds in a liquid composition, such as a lotion, will be from about 0.1-25% by weight, or from about 0.5-10% by weight. The concentration in a semi-solid or solid composition such as a gel or a powder can be about 0.1-5% by weight, or about 0.5-2.5% by weight.

The amount of the 5, 6, or 7-substituted-3-(hetero)arylisoquinolinamine compounds required for use in treatment will vary depending on the particular salt selected and with the route of administration, the nature of the condition being treated and the age and condition of the patient, and will be ultimately at the discretion of the attendant physician or clinician.

Effective dosages and routes of administration of agents of the invention are conventional. The exact amount (effective dose) of the 5, 6, or 7-substituted-3-(hetero)arylisoquinolinamine compound will vary from subject to subject, depending on, for example, the species, age, weight and general or clinical condition of the subject, the severity or mechanism of any disorder being treated, the particular agent or vehicle used, the method and scheduling of administration, and the like. A therapeutically effective dose can be determined empirically, by conventional procedures known to those of skill in the art. See, e.g., *The Pharmacological Basis of Therapeutics*, Goodman and Gilman, eds., Macmillan Publishing Co., New York. For example, an effective dose can be estimated initially either in cell culture assays or in suitable animal models. The animal model may also be used to determine the appropriate concentration ranges and routes of administration. Such information can then be used to determine useful doses and routes for administration in humans. A therapeutic dose can also be selected by analogy to dosages for comparable therapeutic agents.

The particular mode of administration and the dosage regimen will be selected by the attending clinician, taking into account the particulars of the case (e.g., the subject, the disease, the disease state involved, and whether the treatment is prophylactic). Treatment may involve daily or multi-daily doses of compound(s) over a period of a few days to months, or even years.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, 6 to 90 mg/kg/day, or in the range of 15 to 60 mg/kg/day. For example, suitable doses may be 0.5, 5, 10, 25, 50, 100, 250 or 500 mg/kg of body weight per day.

The 5, 6, or 7-substituted-3-(hetero)arylisoquinolinamine compounds are conveniently administered in unit dosage form; for example, containing 5 to 1000 mg, 10 to 750 mg, or 50 to 500 mg of active ingredient per unit dosage form.

The 5, 6, or 7-substituted-3-(hetero)arylisoquinolinamine compounds can be administered to achieve peak plasma concentrations of from about 0.5 to about 75 µM, about 1 to 50 µM, or, about 2 to about 30 µM. Exemplary desirable plasma concentrations include at least or no more than 0.25, 0.5, 1, 5, 10, 25, 50, 75, 100 or 200 µM. This may be achieved, for example, by the intravenous injection of a 0.05 to 5% solution of the 5, 6, or 7-substituted-3-(hetero)arylisoquinolinamine compounds, optionally in saline, or orally administered as a bolus containing about 1-100 mg of the 5, 6, or 7-substituted-3-(hetero)arylisoquinolinamine compounds. Desirable blood levels may be maintained by continuous infusion to provide about 0.01-5.0 mg/kg/hr, for example at least or no more than 0.005, 0.01, 0.1, 2.5, 5.0 or 10.0 mg/kg/hr. Alternatively, such levels can be obtained by intermittent infusions containing about 0.4-15 mg/kg, for example at least or no more than 0.25, 0.5, 1.0, 5.0, 10.0, 15.0 or 25.0 mg/kg of the 5, 6, or 7-substituted-3-(hetero)arylisoquinolinamine compounds.

The 5, 6, or 7-substituted-3-(hetero)arylisoquinolinamine compounds may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Targeting 5, 6, or 7-substituted-3-(hetero)arylisoquinolinamines to Cells

In an exemplary embodiment, the 5, 6, or 7-substituted-3-(hetero)arylisoquinolinamine compound is targeted to cells where treatment is desired, for example, to human cancer cells. The compound is targeted to the desired cell by conjugation to a targeting moiety that specifically binds the desired cell, thereby directing administration of a conjugated molecule. Useful targeting moieties are ligands which specifically bind cell antigens or cell surface ligands, for example, antibodies against the B cell antigen, CD19 (such as B43) and the like.

To form the conjugates of the invention, targeting moieties are covalently bonded to sites on the 5, 6, or 7-substituted-3-(hetero)arylisoquinolinamine compound. The targeting moiety, which is often a polypeptide molecule, is bound to compounds of the invention at reactive sites, including $NH_2$, SH, CHO, COOH, and the like. Specific linking agents are used to join the compounds. Linking agents are chosen according to the reactive site to which the targeting moiety is to be attached.

Methods for selecting an appropriate linking agent and reactive site for attachment of the targeting moiety to the compound of the invention are known, and are described, for example, in Hermanson, et al., Bioconjugate Techniques, Academic Press, 1996; Hermanson, et al., Immobilized Affinity Ligand Techniques, Academic Press, 1992; and Pierce Catalog and Handbook, 1996, pp. T155-T201.

EXAMPLES

The invention may be further clarified by reference to the following Examples, which serve to exemplify some of the preferred embodiments, and not to limit the invention in any way.

Examples 1-3

Synthesis of Isoquinolinamine Derivatives

All chemicals were reagent grade and were purchased from Aldrich Chemical Company (Milwaukee, Wis.) or Sigma Chemical Company (St. Louis, Mo.) or Trans World Chemicals (Rockville, Md.). Solvents were routinely distilled prior to use. Anhydrous THF was distilled from sodium/benzophenone prior to use.

Melting points were determined on an Electrothermal IA9200 melting point apparatus and are uncorrected. Nuclear magnetic resonance spectra were recorded on a Varian 300 spectrometer, using tetramethylsilane (TMS) as the internal standard at zero ppm; chemical shifts are reported in parts per million (ppm) and coupling constants (J) are given in hertz and the abbreviations s, d, t, q, and m refer to singlet, doublet, triplet, quartet and multiplet, respectively.

IR spectra were recorded on a Perkin-Elmer 783 spectrometer and a Nicolet instrument using KBr pellets. Elemental analyses were performed on a CaHo Erba elemental analyzer. Column chromatography was performed on Merck silica gel 60 (70~230 mesh). TLC was carried out using plates coated with silica gel 60F254 purchased from Merck Co.

Example 1

General Synthetic Procedure for Compound 1 to Compound 12

Compound 1 to Compound 12 were synthesized and characterized as discussed in Scheme 1. The structures and physical data are shown below:

Scheme 1

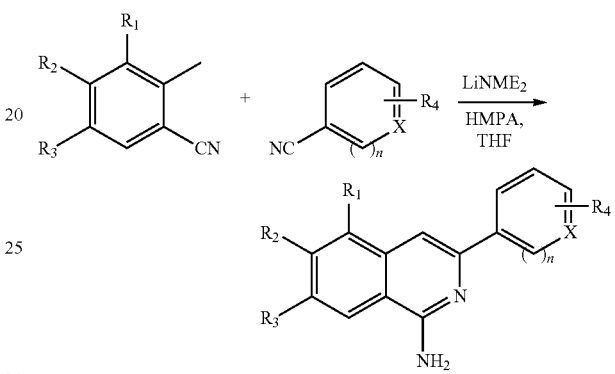

TABLE 1

| Compound # | $R_1$ | $R_2$ | $R_3$ | n | X | $R_4$ |
|---|---|---|---|---|---|---|
| 1 | H | H | H | 1 | C | 2-chloro |
| 2 | H | H | H | 1 | C | 3-chloro |
| 3 | H | H | H | 1 | C | 4-chloro |
| 4 | H | H | H | 1 | C | 3-methoxy |
| 5 | H | H | H | 1 | C | 3,4-dimethoxy |
| 6 | H | H | H | 1 | C | 3,4-methylenedioxide |
| 7 | H | H | H | 1 | N | H |
| 8 | H | H | H | 0 | S | H |
| 9 | H | H | H | 0 | O | H |
| 10 | H | H | Cl | 1 | C | 5-chloro-2-methyl |
| 11 | H | —$OCH_3$ | H | 1 | C | H |
| 12 | H | —$OCH_3$ | H | 1 | C | 3,4-dimethoxy |

Preparation of 3-(2-chlorophenyl)isoquinolin-1-amine (Compound 1)—To dry THF (20 mL) was added $LiNMe_2$ (5 mL of 5% suspension in hexane, 3.3 mmol) at −70° C. After the addition of HMPA (590 mg, 3.3 mmol), the reaction mixture was treated with a solution of o-tolunitrile (350 mg, 3 mmol) in dry THF (10 mL). The resultant red-violet solution was stirred for 30 min, and then treated with a solution of 2-chlorobenzonitrile (825 mg, 6 mmol) in THF. The reaction mixture was heated at 60° C. for 1 h and hydrolyzed using 10% HCl (20 mL). The resulting suspension of the hydrochloride salt was washed with three portions of diethyl ether. The suspension was then neutralized with NaOH and extracted with ethyl acetate. The combined organic extracts were washed with water and dried over sodium sulfate. After removing the solvent, the residue was purified by column chromatography with n-hexane-ethyl acetate (1:1) to afford 1-amino compound. To a solution of 1-amino compound in acetone (5 mL) was added c-HCl to afford the precipitate. The precipitate was collected and washed with acetone to give the amine hydrochloride salt (183.4 mg, 21%). $^1$H NMR (300 MHz, CDCl$_3$) δ: 7.80-7.29 (m, 9H), 5.41 (s, 2H).

The following compounds 2 to 12 were prepared according to a manner similar to that in compound 1.

Preparation of 3-(3-chlorophenyl)isoquinolin-1-amine (Compound 2)—Reaction of o-tolunitrile with 3-chlorobenzonitrile gave compound 2 (white solid, 53%). $^1$H NMR (300 MHz, CDCl$_3$) δ: 8.05-7.29 (m, 9H), 5.49 (s, 2H).

Preparation of 3-(4-chlorophenyl)isoquinolin-1-amine (Compound 3)—Reaction of o-tolunitrile with 4-chlorobenzonitrile gave compound 3 (white solid, 32%). $^1$H NMR (300 MHz, CDCl$_3$) δ: 8.00 (m, 2H), 7.78 (m, 2H), 7.61 (m, 1H), 7.49-7.40 (m, 4H), 5.26 (s, 2H)

Preparation of 3-(3-methoxyphenyl)isoquinolin-1-amine (Compound 4)—Reaction of o-tolunitrile with 3-methoxybenzonitrile gave compound 4 (white solid, 36%). $^1$H NMR (300 MHz, CDCl$_3$) δ: 7.99 (d, 1H), 7.95-7.30 (m, 7H), 6.96 (d, 1H), 5.26 (s, 2H), 3.90 (s, 3H).

Preparation of 3-(3,4-dimethoxyphenyl)isoquinolin-1-amine (Compound 5)—Reaction of o-tolunitrile with 3,4-dimethoxybenzonitrile gave compound 5 (yellow solid, 52%). $^1$H NMR (300 MHz, CDCl$_3$) δ: 8.04 (d, 1H), 7.71-7.46 (m, 5H), 7.21 (s, 1H), 6.96 (d, 1H), 5.24 (s, 2H), 4.02 (s, 3H), 3.94 (s, 3H).

Preparation of 3-(benzo[d][1,3]dioxol-6-yl)isoquinolin-1-amine (Compound 6)—Reaction of o-tolunitrile with benzo[1,3]dioxole-5-carbonitrile gave compound 6 (yellow solid, 30%). $^1$H NMR (300 MHz, CDCl$_3$) δ: 7.71 (m, 2H), 7.59-7.54 (m, 3H), 7.40 (m, 1H), 7.35 (s, 1H), 6.89 (m, 1H), 5.98 (s, 2H), 5.25 (s, 2H).

Preparation of 3-(pyridin-3-yl)isoquinolin-1-amine (Compound 7)—Reaction of o-tolunitrile with 3-cyanopyridine gave compound 7 (yellow solid, 62%). $^1$H NMR (300 MHz, CDCl$_3$) δ: 9.24 (s, 1H), 8.58 (d, 1H), 8.32 (m, 1H), 7.81-7.45 (m, 6H), 5.57 (s, 2H).

Preparation of 3-(thiophen-2-yl)isoquinolin-1-amine (Compound 8)—Reaction of o-tolunitrile with thiophene-2-carbonitrile gave compound 8 (yellow solid, 20%). $^1$H NMR (300 MHz, CDCl$_3$) δ: 7.58 (m, 3H), 7.49 (m, 1H), 7.35 (s, 1H), 7.29 (m, 2H), 7.07 (m, 1H), 5.35 (s, 2H).

Preparation of 3-(furan-2-yl)isoquinolin-1-amine (Compound 9)—Reaction of o-tolunitrile with 2-furonitrile gave compound 9 (yellow solid, 20%). $^1$H NMR (300 MHz, CDCl$_3$) δ: 7.73-7.70 (m, 2H), 7.49-7.57 (m, 2H), 7.43 (s, 1H), 7.26 (m, 1H), 6.99 (m, 1H), 6.47 (m, 1H), 5.47 (s, 2H).

Preparation of 7-chloro-3-(5-chloro-2-methylphenyl)isoquinolin-1-amine (Compound 10)—Reaction of 5-chlor-2-methylbenzonitrile with 5-chloro-2-methylbenzonitrile gave compound 10 (yellow solid, 22%). NMR (300 MHz, CDCl$_3$) δ: 7.81 (s, 1H), 7.68 (d, 1H), 7.61 (d, 1H), 7.44 (d, 1H), 7.23 (m, 2H), 7.09 (s, 1H), 5.19 (s, 2H), 2.53 (s, 3H).

Preparation of 6-methoxy-3-phenylisoquinolin-1-amine (Compound 11)—Reaction of 4-methoxy-2-methylbenzonitrile with benzonitrile gave compound 11 (yellow solid, 33%). $^1$H NMR (300 MHz, CDCl$_3$) δ: 8.02 (m, 2H), 7.57 (d, 1H), 7.44-7.30 (m, 4H), 6.93 (m, 2H), 5.40 (s, 2H), 3.79 (s, 3H).

Preparation of 6-methoxy-3-(3,4-dimethoxyphenyl)isoquinolin-1-amine (Compound 12)—Reaction of 4-methoxy-2-methylbenzonitrile with 3,4-dimethoxybenzonitrile gave compound 12 (yellow solid, 35%). $^1$H NMR (300 MHz, CDCl$_3$) δ: 7.72 (s, 1H), 7.60-7.52 (m, 2H), 7.25 (s, 1H), 6.92-6.81 (m, 3H), 5.69 (s, 2H), 3.87 (s, 3H), 3.77 (s, 3H), 3.74 (s, 3H).

Example 2

Synthesis of Substituted 2-methyl-N,N-dimethylbenzamides

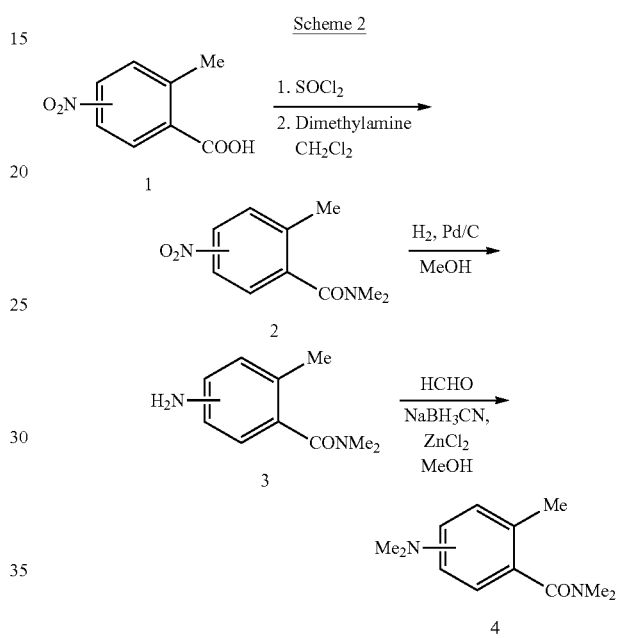

a) Preparation of 2,N,N-trimethyl-5-nitrobenzamide (2)

The preparation of 2,N,N-trimethyl-5-nitrobenzamide utilized the procedure described in U.S. Pat. No. 4,942,163. The reaction mixture of 2-methyl-5-nitrobenzoic acid (5 g, 27.6 mmol) and thionyl chloride (16.4 g, 138 mmol) was refluxed overnight. The excess thionyl chloride was removed by vacuum distillation to afford 2-methyl-5-nitro-benzoyl chloride as a solid residue. This material was dissolved in methylene chloride (30 mL) and added dropwise with stirring to a commercial 40% dimethylamine solution (30 g, 270 mmol) maintaining the temperature at 0 to 12° C. After complete addition, the reaction mixture was stirred at room temperature for 2 h. The reaction mixture was diluted with water and extracted with methylene chloride. The combined organic extracts were washed with water, dried and concentrated. The residue was purified by column chromatography with n-hexane-ethyl acetate (3:1) to afford amide as a solid (5.46 g, 95%). The identity was verified by $^1$H NMR b) Preparation of 5-amino-2,N,N-trimethylbenzamide (3)

A solution of amide (5.45 g, 26.2 mmol) in methanol (30 mL) was hydrogenated overnight under 60 psi H$_2$ in the presence of 5% Pd/C (0.3 g) using Parr hydrogenation apparatus. The reaction mixture was filtered through Celite and the filter cake was washed with methanol. After concentration, the residue was purified by column chromatography with n-hexane-ethyl acetate (1:1) to afford compound as a solid (4.63 g, 99%). The identity was verified by $^1$H NMR c) Preparation of 5-dimethylamino-2,N,N-trimethylbenzamide (4)

To a solution of amine (4.63 g, 26 mmol) and HCHO (7.02 g, 78 mmol) in methanol (40 mL) at 0° C. was added dropwise a solution of NaBH$_3$CN (3.22 g, 52 mmol) and ZnCl$_2$ (3.53 g, 26 mmol) in methanol (30 mL). After complete addition, the reaction mixture was warmed to room temperature. The reaction mixture was quenched with 1.0 N NaOH (100 mL) and the methanol was removed. The residue was extracted with ethyl acetate, and the combined organic extracts were washed with water, dried and concentrated. The residue was purified by column chromatography with n-hexane-ethyl acetate (3:1) to afford amide as an oil (5.04 g, 94%). The identity was verified by $^1$H NMR Other 3 or 4-dimethylamino-2,N,N-trimethylbenzamide were prepared according to a manner similar to that in 5-dimethylamino-2,N,N-trimethylbenzamide (4). The synthesis of 3-dimethylamino-2,N,N-trimethylbenzamide is described in Bioorganic & Medicinal Chemistry paper (vol. 6, 2449 (1998)). The synthesis of 4-dimethylamino-2,N,N-trimethylbenzamide is described in WO 2005/075432. And the synthesis of 5-dimethylamino-2,N,N-trimethylbenzamide is described in U.S. Pat. No. 4,942,163.

Example 3

Synthesis of Compound 13 to Compound 56

Compound 13 to Compound 56 were synthesized and characterized as discussed in Scheme 3. The structures and physical data are shown below:

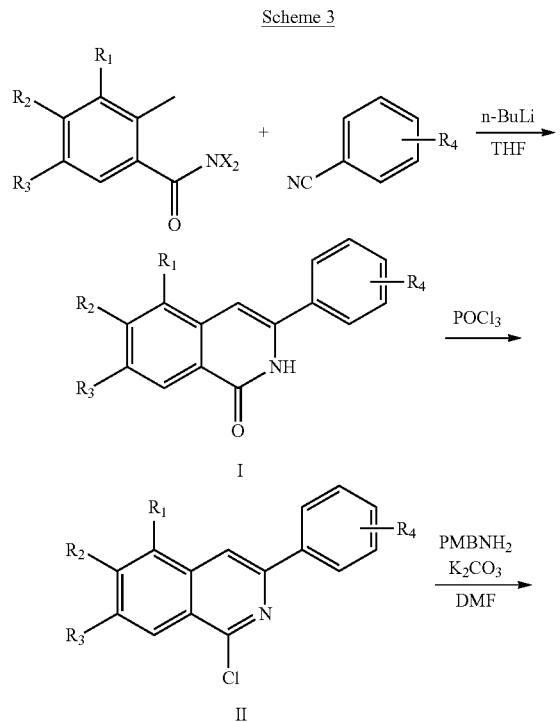

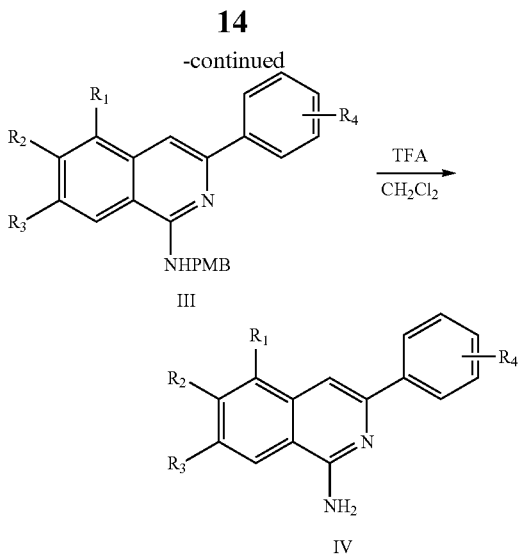

X = Methyl or Ethyl

TABLE 2

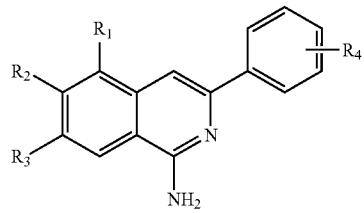

| Compound # | R$_1$ | R$_2$ | R$_3$ | R$_4$ |
|---|---|---|---|---|
| 13 | H | H | —N(CH$_3$)$_2$ | 3-methoxy |
| 14 | H | H | —N(CH$_3$)$_2$ | 3-methyl |
| 15 | H | H | —N(CH$_3$)$_2$ | 3,4-dimethoxy |
| 16 | H | H | —N(CH$_3$)$_2$ | 3,5-dimethoxy |
| 17 | —N(CH$_3$)$_2$ | H | H | H |
| 18 | —N(CH$_3$)$_2$ | H | H | 2-methyl |
| 19 | —N(CH$_3$)$_2$ | H | H | 3,4-dimethoxy |
| 20 | —N(CH$_3$)$_2$ | H | H | 2,6-dimethyl |
| 21 | H | —N(CH$_3$)$_2$ | H | 3-methoxy |
| 22 | —CH$_3$ | H | H | 3,4-dimethoxy |
| 23 | H | —CH$_3$ | H | 2-methyl |
| 24 | H | —CH$_3$ | H | 2-methoxy |
| 25 | H | —CH$_3$ | H | 3-methoxy |
| 26 | H | —CH$_3$ | H | 4-methoxy |
| 27 | H | —CH$_3$ | H | 3,4-dimethoxy |
| 28 | H | —CH$_3$ | H | 3,4-methylendioxide |
| 29 | H | —CH$_3$ | H | 4-ethoxy |
| 30 | H | —CH$_3$ | H | 3,5-dimethoxy |
| 31 | H | —CH$_3$ | H | 4-methoxy-2-methyl |
| 32 | H | —CH$_3$ | H | 3,4,5-trimethoxy |
| 33 | H | —CH$_3$ | H | 2-fluoro |
| 34 | H | —CH$_3$ | H | 2,6-dimethyl |
| 35 | H | —CH$_3$ | H | 3-methyl |
| 36 | H | —CH$_3$ | H | 4-methyl |
| 37 | H | H | —CH$_3$ | 2-methoxy |
| 38 | H | H | —CH$_3$ | 3-methoxy |
| 39 | H | H | —CH$_3$ | 4-methoxy |
| 40 | H | H | —CH$_3$ | 4-ethoxy |
| 41 | H | H | —CH$_3$ | 2-fluoro |
| 42 | H | H | —CH$_3$ | 4-methoxy-2-methyl |
| 43 | H | H | —CH$_3$ | 2,6-dimethyl |
| 44 | H | H | —CH$_3$ | 3,4-dimethoxy |
| 45 | H | H | —CH$_3$ | 3,4-methylendioxide |
| 46 | H | H | —CH$_3$ | 3,5-dimethoxy |
| 47 | H | H | —CH$_3$ | 3,4,5-trimethoxy |
| 48 | H | H | —CH$_3$ | 2-methyl |
| 49 | H | H | —CH$_3$ | 3-methyl |
| 50 | H | H | —CH$_3$ | 5-methoxy-2-methyl |

TABLE 2-continued

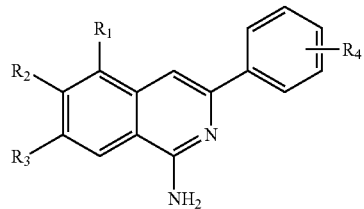

| Compound # | $R_1$ | $R_2$ | $R_3$ | $R_4$ |
|---|---|---|---|---|
| 51 | H | —OCH$_3$ | —OCH$_3$ | H |
| 52 | H | —OCH$_3$ | —OCH$_3$ | 3-methoxy |
| 53 | H | —OCH$_3$ | —OCH$_3$ | 2,6-dimethyl |
| 54 | H | —OCH$_3$ | —OCH$_3$ | 3-methyl |
| 55 | H | —OCH$_3$ | —OCH$_3$ | 3,5-dimethoxy |
| 56 | H | —OCH$_3$ | —OCH$_3$ | 2-methyl |

Preparation of 3-(3-methoxyphenyl)-$N^7$,$N^7$-dimethylisoquinoline-1,7-diamine hydrochloride (compound 13)

a) 7-Dimethylamino-3-(3-methoxyphenyl)-2H-isoquinolin-1-one (I)

To a solution of diisopropylamine (1.5 g, 15 mmol) in dry THF (10 mL) was added n-BuLi (6 mL of 2.5 M in hexane, 15 mmol) at −78° C. After 30 min, a solution of 5-dimethylamino-2,N,N-trimethylbenzamide (2.06 g, 10 mmol) in THF (15 mL) was added dropwise at −78° C., the red orange solution was stirred at the same temperature for 1 h. The solution of 3-methoxybenzonitrile (1.7 g, 13 mmol) in dry TIM (10 mL) were added and the reaction mixture was stirred at −78° C. for 2 h. The reaction solution was quenched with water and extracted with ethyl acetate and dried over sodium sulfate. After removing the solvent, the residue was purified by column chromatography with n-hexane-ethyl acetate (3:1) to afford compound I as yellow solid (596 mg, 20%). $^1$H NMR (300 MHz, CDCl$_3$) δ: 9.73 (s, 1H), 7.61 (s, 1H), 7.50 (d, J=8.7 Hz, 1H), 7.38 (m, 1H), 7.23-7.22 (m, 3H), 6.96 (m, 1H), 6.74 (s, 1H), 3.90 (s, 3H), 3.09 (s, 6H).

b) [1-Chloro-3-(3-methoxyphenyl)isoquinolin-7-yl]dimethylamine (II)

A reaction mixture of 3-aryl isoquinolinone I (550 mg, 1.9 mmol) and POCl$_3$ (10 mL) was stirred at 50° C. overnight. The POCl$_3$ was removed by vacuum distillation and the residue was extracted with ethyl acetate. The combined organic layers were washed with water, brine and dried over sodium sulfate. After removing the solvent, the residue was purified by column chromatography with n-hexane-ethyl acetate (3:1) to afford compound II as yellow solid (530 mg, 90%). $^1$H NMR (300 MHz, CDCl$_3$) δ: 7.85 (s, 1H), 7.72 (d, J=8.7 Hz, 1H), 7.64-7.62 (m, 2H), 7.39-7.35 (m, 2H), 7.22 (d, J=2 Hz, 1H), 6.92 (m, 1H), 3.91 (s, 3H), 3.13 (s, 6H).

c) $N^1$-(4-Methoxybenzyl)-3-(3-methoxyphenyl)-$N^7$,$N^7$-dimethylisoquinoline-1,7-diamine (III)

A mixture of 1-chloroimine isoquinoline II (500 mg, 1.6 mmol), 4-methoxy benzylamine (877 mg, 6.4 mmol), and potassium carbonate (2 g, 15 mmol) in DMF was refluxed overnight. The reaction mixture was cooled to room temperature, diluted with water, and extracted with ethyl acetate. The combined organic extracts were washed with water, dried, and concentrated. The residue was purified by column chromatography on silica gel with n-hexane-ethyl acetate (3:1) to afford compound III (310 mg, 47%). $^1$H NMR (300 MHz, CDCl$_3$) δ: 7.74-7.62 (m, 3H), 7.45-7.33 (m, 4H), 7.22 (m, 1H), 6.92 (m, 3H), 6.66 (m, 1H), 5.24 (s, 1H), 4.91 (d, 2H), 3.91 (s, 3H), 3.85 (s, 3H), 3.09 (s, 6H).

d) 3-(3-methoxyphenyl)-$N^7$,$N^7$-dimethylisoquinoline-1,7-diamine hydrochloride (IV, compound 13)

A reaction mixture of $N^1$-(4-methoxy benzyl)-isoquinolinamine compound III (300 mg, 0.73 mmol) and trifluoroacetic acid (5 mL) in methylene chloride (5 mL) was refluxed for 2 days. A solution of NaHCO$_3$ was added and the reaction mixture was extracted with methylene chloride. The combined organic extracts were washed with water, dried, and concentrated. The residue was purified by column chromatography on silica gel with n-hexane-ethyl acetate (1:1) to afford 1-amino isoquinoline (151 mg, 71%). The 1-amino compound was dissolved in acetone (5 mL) and 5 drops of concentrated HCl was added. The hydrochloride salt was filtered and filter cake was washed with acetone. After drying, 120 mg of 1-amino isoquinoline hydrochloride was obtained (Compound 13, 50%). $^1$H NMR (300 MHz, DMSO-d6) δ: 13.57 (s, 1H), 9.37 (s, 2H), 7.79 (d, 1H), 7.55-7.39 (m, 6H), 7.02 (m, 1H), 3.87 (s, 3H), 3.06 (s, 6H).

The following compounds 14 to 56 were prepared according to a manner similar to that in compound 13, except that diisopropylamine was not utilized in step (a) for the preparation of compounds 22-56.

$N^7$,$N^7$-Dimethyl-3-m-tolylisoquinoline-1,7-diamine hydrochloride (Compound 14)—Reaction of 5-dimethylamino-2,N,N-trimethylbenzamide with m-tolunitrile gave Compound 14 (yellow solid, 62%). $^1$H NMR (300 MHz, CDCl$_3$) δ: 7.85 (s, 1H), 7.80 (d, 1H), 7.63 (d, 1H), 7.38 (s, 1H), 7.35-7.24 (m, 2H), 7.15 (m, 1H), 6.76 (m, 1H), 5.30 (s, 2H), 3.06 (s, 6H), 2.43 (s, 3H).

3-(3,4-Dimethoxyphenyl)-$N^7$,$N^7$-dimethylisoquinoline-1,7-diamine hydrochloride (Compound 15)—Reaction of 5-dimethylamino-2,N,N-trimethylbenzamide with 3,4-dimethoxybenzonitrile gave Compound 15 (yellow solid, 63%). $^1$H NMR (300 MHz, DMSO-d6) δ: 13.56 (s, 1H), 9.34 (s, 2H), 7.75 (d, 1H), 7.58-7.46 (m, 5H), 7.06 (d, 1H), 3.90 (s, 3H), 3.85 (s, 3H), 3.06 (s, 6H).

3-(3,5-Dimethoxyphenyl)-$N^7$,$N^7$-dimethylisoquinoline-1,7-diamine hydrochloride (Compound 16)—Reaction of 5-dimethylamino-2,N,N-trimethylbenzamide with 3,5-dimethoxybenzonitrile gave Compound 16 (yellow solid, 76%). $^1$H NMR (300 MHz, DMSO-d6) δ: 13.50 (s, 1H), 9.31 (s, 2H), 7.79 (d, 1H), 7.59 (s, 1H), 7.54-7.47 (m, 2H), 7.14 (d, 2H), 6.58 (t, 1H), 3.84 (s, 6H), 3.07 (s, 61-1).

$N^5$,$N^5$-Dimethyl-3-phenylisoquinoline-1,5-diamine (Compound 17)—Reaction of 3-dimethylamino-2,N,N-trimethylbenzamide with benzonitrile gave Compound 17 (yellow solid, 73%). $^1$H NMR (300 MHz, CDCl$_3$) δ: 8.08 (m, 2H), 7.82 (s, 1H), 7.48-7.33 (m, 5H), 7.18 (m, 2H), 5.24 (s, 2H), 2.89 (s, 6H).

$N^5$,$N^5$-Dimethyl-3-o-tolylisoquinoline-1,5-diamine (Compound 18)—Reaction of 3-dimethylamino-2,N,N-trimethylbenzamide with o-tolunitrile gave Compound 18 (yellow solid, 60%). $^1$H NMR (300 MHz, DMSO-d6) δ: 13.87 (s, 1H), 8.42 (d, 1H), 7.82-7.71 (m, 2H), 7.50-7.33 (m, 5H), 2.91 (s, 6H), 2.42 (s, 3H).

3-(3,4-Dimethoxyphenyl)-$N^5$,$N^5$-dimethylisoquinoline-1,5-diamine (Compound 19)—Reaction of 3-dimethylamino-2,N,N-trimethylbenzamide with 3,4-dimethoxybenzonitrile gave Compound 19 (yellow solid, 40%). $^1$NMR (300 MHz, DMSO-d6) δ: 9.69 (s, 2H), 8.40 (d, 1H), 7.93-7.91 (m, 2H), 7.75-7.67 (m, 3H), 7.13 (d, 1H), 3.94 (s, 3H), 3.82 (s, 3H), 3.03 (s, 6H).

$N^5$,$N^5$-Dimethyl-3-(2,6-dimethylphenyl)isoquinoline-1,5-diamine (Compound 20)—Reaction of 3-dimethylamino-2,N,N-trimethylbenzamide with 2,6-dimethylbenzonitrile gave Compound 20 (yellow solid, 60%). $^1$H NMR (300 MHz, CDCl$_3$) δ: 7.46-7.41 (m, 2H), 7.29-7.09 (m, 5H), 5.58 (s, 2H), 2.83 (s, 6H), 2.14 (s, 6H).

3-(3-Methoxyphenyl)-N$^6$,N$^6$-dimethyl-isoquinoline-1,6-diamine (Compound 21)—Reaction of 4-dimethylamino-2,N,N-trimethylbenzamide with 3-methoxybenzonitrile gave Compound 21 (brown solid, 35%). $^1$H NMR (300 MHz, DMSO-d6) δ: 7.70 (d J=8.4 Hz, 1H), 7.57-7.51 (m, 2H), 7.38 (d J=8.4 Hz, 1H), 7.22 (s, 1H), 7.03 (dd, J=8.1 Hz, J=2.8 Hz, 1H), 6.94 (m, 1H), 6.74 (d, J=2.8 Hz, 1H), 3.86 (s, 3H), 3.11 (s, 6H).

3-(3,4-Dimethoxyphenyl)-5-methylisoquinolin-1-amine (Compound 22)—Reaction of N,N-diethyl-2,3-dimethylbenzamide with 3,4-dimethoxybenzonitrile gave Compound 22 (yellow solid, 65%). $^1$H NMR (300 MHz, CDCl$_3$) δ: 7.70 (m, 1H), 7.57-7.62 (m, 2H), 7.48 (s, 1H), 7.40 (m, 1H), 7.28 (m, 1H), 6.94 (d, J=8.4 Hz, 1H), 5.42 (s, 2H), 3.98 (s, 3H), 3.88 (s, 3H), 2.63 (s, 3H).

6-Methyl-3-o-tolylisoquinolin-1-amine hydrochloride salt (Compound 23)—Reaction of N,N-diethyl-2,4-dimethylbenzamide with o-tolunitrile gave Compound 23 (yellow solid, 67%). Mp 269.1-270.2° C. IR (cm$^{-1}$): 3300, 1650. $^1$H NMR (DMSO-d6) δ: 13.84 (s, 1H), 9.40 (s, 1H), 8.79-7.57 (m, 7H), 7.38 (s, 1H), 2.75 (s, 3H), 2.61 (s, 3H). $^{13}$C NMR (DMSO-d6) δ: 153.4, 144.4, 137.0, 135.9, 134.8, 131.6, 129.4, 128.7, 128.5, 128.4, 125.7, 124.8, 124.0, 113.0, 109.5. MS, m/e (%): 248 (M+, 100), 232 (87), 230 (54). Anal. C$_{17}$H$_{17}$ClN$_2$ (C, H, N) Calc'd: 71.70; 6.02; 9.84. Found: 71.58; 6.27; 9.58.

3-(2-Methoxyphenyl)-6-methylisoquinolin-1-amine (Compound 24)—Reaction of N,N-diethyl-2,4-dimethylbenzamide with 2-methoxybenzonitrile gave Compound 24 (yellow solid, 64%). $^1$H NMR (300 MHz, CDCl$_3$) δ: 8.03 (d, J=8.5 Hz, 1H), 7.64 (m, 1H), 7.45 (s, 1H), 7.35-7.23 (m, 3H), 7.05-6.97 (m, 2H), 3.88 (s, 3H), 2.47 (s, 3H).

3-(3-Methoxyphenyl)-6-methylisoquinolin-1-amine (Compound 25)—Reaction of N,N-diethyl-2,4-dimethylbenzamide with 3-methoxybenzonitrile gave Compound 25 (yellow solid, 68%). $^1$H NMR (300 MHz, CDCl$_3$) δ: 7.67-7.59 (m, 3H), 7.51 (s, 1H), 7.38-7.24 (m, 3H), 6.94-6.90 (m, 1H), 5.26 (bs, 2H), 3.88 (s, 3H), 2.48 (s, 3H).

3-(4-Methoxyphenyl)-6-methylisoquinolin-1-amine (Compound 26)—Reaction of N,N-diethyl-2,4-dimethylbenzamide with 4-methoxybenzonitrile gave Compound 26 (yellow solid, 60%). $^1$H NMR (300 MHz, CDCl$_3$) δ: 8.04 (d, J=8.1 Hz, 2H), 7.65 (d, J=8.5 Hz, 1H), 7.42 (s, 1H), 7.24 (s, 1H), 7.17 (d, J=8.2 Hz, 1H), 6.95 (d, J=8.5 Hz, 2H), 3.81 (s, 3H), 2.43 (s, 3H).

3-(3,4-Dimethoxyphenyl)-6-methylisoquinolin-1-amine (Compound 27)—Reaction of N,N-diethyl-2,4-dimethylbenzamide with 3,4-dimethoxybenzonitrile gave Compound 27 (yellow solid, 79%). $^1$H NMR (300 MHz, CDCl$_3$) δ: 7.67-7.64 (m, 2H), 7.54 (m, 1H), 7.45 (s, 1H), 7.27 (s, 1H), 7.18 (m, 1H), 6.91 (d, J=8.5 Hz, 1H), 5.76 (s, 2H), 3.96 (s, 3H), 3.89 (s, 3H), 2.50 (s, 3H).

3-(Benzo[d][1,3]dioxol-6-yl)-6-methylisoquinolin-1-amine (Compound 28)—Reaction of N,N-diethyl-2,4-dimethylbenzamide with benzo[1,3]dioxole-5-carbonitrile gave Compound 28 (yellow solid, 71%). $^1$H NMR (300 MHz, CDCl$_3$) δ: 7.63 (d, J=8.5 Hz, 1H), 7.54 (m, 2H), 7.45 (s, 1H), 7.22 (m, 2H), 6.88 (d, J=8.5 Hz, 1H), 5.98 (s, 2H), 5.40 (s, 2H), 2.46 (s, 3H).

3-(4-Ethoxyphenyl)-6-methylisoquinolin-1-amine (Compound 29)—Reaction of N,N-diethyl-2,4-dimethylbenzamide with 4-ethoxybenzonitrile gave Compound 29 (yellow solid, 67%). $^1$H NMR (300 MHz, CDCl$_3$) δ: 7.96 (m, 2H), 7.66 (d, J=8.5 Hz, 1H), 7.47 (s, 1H), 7.30 (s, 1H), 7.23 (m, 1H), 6.97 (m, 2H), 5.36 (s, 2H), 4.05 (q, J=7.0 Hz, 2H), 2.48 (s, 3H), 1.43 (t, J=7.0 Hz, 3H).

3-(3,5-Dimethoxyphenyl)-6-methylisoquinolin-1-amine (Compound 30)—Reaction of N,N-diethyl-2,4-dimethylbenzamide with 3,5-dimethoxybenzonitrile gave Compound 30 (yellow solid, 90%). $^1$H NMR (300 MHz, DMSO-d6) δ: 8.42 (d, J=8.5 Hz, 1H), 7.72 (s, 1H), 7.60 (m, 2H), 7.11 (m, 2H), 6.62 (s, 1H), 3.45 (s, 6H), 2.49 (s, 3H).

3-(4-Methoxy-2-methylphenyl)-6-methylisoquinolin-1-amine (Compound 31)—Reaction of N,N-diethyl-2,4-dimethylbenzamide with 4-methoxy-2-methylbenzonitrile gave Compound 31 (yellow solid, 67%). $^1$H NMR (300 MHz, CDCl$_3$) δ: 7.97 (d, J=8.5 Hz, 1H), 7.42 (s, 1H), 7.37-7.28 (m, 2H), 7.15-6.91 (b, 2H), 6.85 (s, 1H), 6.76 (m, 2H), 3.78 (s, 3H), 2.47 (s, 3H), 2.37 (s, 3H).

3-(3,4,5-Trimethoxyphenyl)-6-methylisoquinolin-1-amine (Compound 32)—Reaction of N,N-diethyl-2,4-dimethylbenzamide with 3,4,5-trimethoxybenzonitrile gave Compound 32 (yellow solid, 26%). $^1$H NMR (300 MHz, CDCl$_3$) δ: 7.73 (d, 1H), 7.54 (s, 1H), 7.32-7.25 (m, 3H), 6.97-6.71 (m, 1H), 5.63 (s, 2H), 4.04 (s, 6H), 3.90 (s, 3H), 2.52 (s, 3H).

3-(2-Fluorophenyl)-6-methylisoquinolin-1-amine (Compound 33)—Reaction of N,N-diethyl-2,4-dimethylbenzamide with 2-fluorobenzonitrile gave Compound 33 (yellow solid, 69%). $^1$H NMR (300 MHz, CDCl$_3$) δ: 8.00 (m, 1H), 7.70 (d, 1H), 7.54 (s, 1H), 7.48 (d, 1H), 7.34-7.14 (m, 4H), 5.39 (s, 2H), 2.51 (s, 3H).

6-Methyl-3-(2,6-dimethylphenyl)isoquinolin-1-amine (Compound 34)—Reaction of N,N-diethyl-2,4-dimethylbenzamide with 2,6-dimethylbenzonitrile gave Compound 34 (yellow solid, 68%). $^1$H NMR (300 MHz, CDCl$_3$) δ: 7.72 (d, 1H), 7.48 (s, 1H), 7.32 (d, 1H), 7.20-7.08 (m, 3H), 6.89 (s, 1H), 5.26 (s, 2H), 2.52 (s, 3H), 2.12 (s, 6H).

6-Methyl-3-m-tolylisoquinolin-1-amine (Compound 35)—Reaction of N,N-diethyl-2,4-dimethylbenzamide with m-tolunitrile gave Compound 35 (white solid, 89%). $^1$H NMR (300 MHz, CDCl$_3$) δ: 9.36 (s, 2H), 8.44 (d, J=8.4 Hz, 1H), 7.83-7.79 (m, 2H), 7.55 (s, 1H), 7.46-7.39 (m, 2H), 7.28 (d, J=8.1 Hz, 1H), 7.14 (s, 1H), 2.57 (s, 3H), 2.46 (s, 3H).

6-Methyl-3-p-tolylisoquinolin-1-amine (Compound 36)—Reaction of N,N-diethyl-2,4-dimethylbenzamide with p-tolunitrile gave Compound 36 (white solid, 75%). $^1$H NMR (300 MHz, CDCl$_3$) δ: 7.94 (d, J=8.1 Hz, 2H), 7.70 (d, J=8.4 Hz, 1H), 7.51 (s, 1H), 7.35 (s, 1H), 7.29-7.24 (m, 3H), 5.43 (s, 2H), 2.50 (s, 3H), 2.40 (s, 3H).

3-(2-Methoxyphenyl)-7-methylisoquinolin-1-amine (Compound 37)—Reaction of 1N,N-diethyl-2,5-dimethylbenzamide with 2-methoxybenzonitrile gave Compound 37 (yellow solid, 38%). $^1$H NMR (300 MHz, CDCl$_3$) δ: 8.00 (s, 1H), 7.63-7.50 (m, 3H), 7.41 (m, 1H), 7.11 (s, 1H), 7.06-7.00 (m, 2H), 3.87 (s, 3H), 2.50 (s, 3H).

3-(3-Methoxyphenyl)-7-methylisoquinolin-1-amine (Compound 38)—Reaction of N,N-diethyl-2,5-dimethylbenzamide with 3-methoxybenzonitrile gave Compound 38 (yellow solid, 92%). $^1$H NMR (300 MHz, CDCl$_3$) δ: 7.74 (s, 1H), 7.61 (d, 1H), 7.54-7.45 (m, 3H), 7.37 (t, 1H), 7.29 (s, 1H), 6.93 (m, 1H), 3.89 (s, 3H), 2.49 (s, 3H).

3-(4-Methoxyphenyl)-7-methylisoquinolin-1-amine (Compound 39)—Reaction of N,N-diethyl-2,5-dimethylbenzamide with 4-methoxybenzonitrile gave Compound 39 (yellow solid, 54%). $^1$H NMR (300 MHz, CDCl$_3$) δ: 7.97 (d, 2H), 7.63 (d, 1H), 7.58 (s, 1H), 7.46 (m, 1H), 7.35 (s, 1H), 6.97 (d, 2H), 3.86 (s, 3H), 2.51 (s, 3H).

3-(4-Ethoxyphenyl)-7-methylisoquinolin-1-amine (Compound 40)—Reaction of N,N-diethyl-2,5-dimethylbenzamide with 4-ethoxybenzonitrile gave Compound 40 (yellow solid, 67%). ¹H NMR (300 MHz, CDCl₃) δ: 7.97 (d, 2H), 7.62 (d, 1H), 7.54 (s, 1H), 7.43 (m, 1H), 7.36 (s, 1H), 6.96 (d, 2H), 5.26 (s, 2H), 4.06 (q, 2H), 2.49 (s, 3H), 1.43 (t, 3H).

3-(2-Fluorophenyl)-7-methylisoquinolin-1-amine (Compound 41)—Reaction of N,N-diethyl-2,5-dimethylbenzamide with 2-fluorobenzonitrile gave Compound 41 (yellow solid, 79%). ¹H NMR (300 MHz, CDCl₃) δ: 8.05 (m, 1H), 7.67 (d, 1H), 7.57 (s, 1H), 7.56 (s, 1H), 7.48 (m, 1H), 7.31-7.06 (m, 3H), 5.17 (s, 2H), 2.52 (s, 3H).

3-(4-Methoxy-2-methylphenyl)-7-methylisoquinolin-1-amine (Compound 42)—Reaction of N,N-diethyl-2,5-dimethylbenzamide with 4-methoxy-2-methylbenzonitrile gave Compound 42 (yellow solid, 90%). ¹H NMR (300 MHz, CDCl₃) δ: 7.93 (s, 2H), 7.57-7.55 (d, 2H), 7.32 (d, 1H), 6.82-6.78 (m, 3H), 3.82 (s, 3H), 2.53 (s, 3H), 2.36 (s, 3H).

7-Methyl-3-(2,6-dimethylphenyl)isoquinolin-1-amine (Compound 43)—Reaction of N,N-diethyl-2,5-dimethylbenzamide with 2,6-dimethylbenzonitrile gave Compound 43 (yellow solid, 68%). ¹H NMR (300 MHz, CDCl₃) δ: 7.63-7.46 (m, 3H), 7.19-7.08 (m, 3H), 6.93 (s, 1H), 5.17 (s, 2H), 2.54 (s, 3H), 2.12 (s, 6H).

3-(3,4-Dimethoxyphenyl)-7-methylisoquinolin-1-amine (Compound 44)—Reaction of N,N-diethyl-2,5-dimethylbenzamide with 3,4-dimethoxybenzonitrile gave Compound 44 (yellow solid, 46%). ¹H NMR (300 MHz, CDCl₃) δ: 7.80 (s, 1H), 7.62 (d, 1H), 7.55-7.46 (m, 3H), 7.19 (s, 1H), 6.94 (d, 1H), 4.02 (s, 1H), 3.93 (s, 3H), 2.52 (s, 3H).

3-(Benzo[d][1,3]dioxol-6-yl)-7-methylisoquinolin-1-amine (Compound 45)—Reaction of N,N-diethyl-2,5-dimethylbenzamide with benzo[1,3]dioxole-5-carbonitrile gave Compound 45 (yellow solid, 70%). ¹H NMR (300 MHz, CDCl₃) δ: 7.62-7.55 (m, 4H), 7.45 (m, 1H), 7.34 (s, 1H), 6.90 (m, 1H), 6.00 (s, 2H), 5.16 (s, 2H), 2.51 (s, 3H).

3-(3,5-Dimethoxyphenyl)-7-methylisoquinolin-1-amine (Compound 46)—Reaction of N,N-diethyl-2,5-dimethylbenzamide with 3,5-dimethoxybenzonitrile gave Compound 46 (yellow solid, 71%). ¹H NMR (300 MHz, CDCl₃) δ: 7.85 (s, 1H), 7.50 (d, 1H), 7.38 (d, 1H), 6.86 (d, 1H), 6.69-6.67 (d, 2H), 3.93 (s, 3H), 3.83 (s, 3H), 2.52 (s, 3H).

3-(3,4,5-Trimethoxyphenyl)-7-methylisoquinolin-1-amine (Compound 47)—Reaction of N,N-diethyl-2,5-dimethylbenzamide with 3,4,5-trimethoxybenzonitrile gave Compound 47 (yellow solid, 95%). ¹H NMR (300 MHz, CDCl₃) δ: 7.66 (d, 1H), 7.57 (s, 1H), 7.48 (d, 1H), 7.40 (s, 1H), 7.29 (s, 2H), 3.96 (s, 6H), 3.89 (s, 3H), 2.52 (s, 3H).

7-Methyl-3-o-tolylisoquinolin-1-amine (Compound 48)—Reaction of N,N-diethyl-2,5-dimethylbenzamide with o-tolunitrile gave Compound 48 (yellow solid, 91%). ¹H NMR (300 MHz, CDCl₃) δ: 7.63-7.58 (m, 2H), 7.47-7.40 (m, 2H), 7.27-7.20 (m, 3H), 7.05 (s, 1H), 5.41 (s, 2H), 2.51 (s, 3H), 2.38 (s, 3H).

7-Methyl-3-m-tolylisoquinolin-1-amine (Compound 49)—Reaction of N,N-diethyl-2,5-dimethylbenzamide with m-tolunitrile gave Compound 49 (yellow solid, 97%). ¹H NMR (300 MHz, CDCl₃) δ: 7.82 (s, 1H), 7.78 (d, J=8.1 Hz, 1H), 7.63-7.58 (m, 2H), 7.43-7.32 (m, 3H), 7.17 (d, J=8.1 Hz, 1H), 5.86 (s, 2H), 2.47 (s, 3H), 2.42 (s, 3H).

3-(5-Methoxy-2-methylphenyl)-7-methyl-isoquinolin-1-amine (Compound 50)—Reaction of N,N-diethyl-2,5-dimethylbenzamide with 5-methoxy-2-methylbenzonitrile gave Compound 50 (yellow solid, 77%). ¹H NMR (300 MHz, CDCl₃) δ: 7.64-7.60 (m, 2H), 7.46 (d, J=8.1 Hz, 1H), 7.46 (d, J=8.1 Hz, 1H), 7.06 (s, 1H), 7.02 (d, J=2.8 Hz, 1H), 6.83 (dd, J=8.1 Hz, J=2.8 Hz, 1H), 5.41 (s, 2H), 3.81 (s, 3H), 2.52 (s, 3H), 2.31 (s, 3H).

6,7-Dimethoxy-3-phenylisoquinolin-1-amine (Compound 51)—Reaction of N,N-diethyl-4,5-dimethoxy-2-methylbenzamide with benzonitrile gave Compound 51 (yellow solid, 71%). ¹H NMR (300 MHz, CDCl₃) δ: 7.97-7.95 (m, 2H), 7.45-7.30 (m, 4H), 7.05 (s, 1H), 6.94 (s, 1H), 5.29 (s, 2H), 3.94 (s, 3H), 3.82 (s, 3H).

6,7-Dimethoxy-3-(3-methoxyphenyl)isoquinolin-1-amine (Compound 52)—Reaction of N,N-diethyl-4,5-dimethoxy-2-methylbenzamide with 3-methoxybenzonitrile gave Compound 52 (yellow solid, 60%). ¹H NMR (300 MHz, CDCl₃) δ: 7.53-7.46 (m, 2H), 7.30 (m, 1H), 7.22 (s, 1H), 7.18 (s, 1H), 6.90 (s, 1H), 6.88 (m, 1H), 3.92 (s, 3H), 3.89 (s, 3H), 3.82 (s, 3H).

6,7-Dimethoxy-3-(2,6-dimethylphenyl)isoquinolin-1-amine (Compound 53)—Reaction of N,N-diethyl-4,5-dimethoxy-2-methylbenzamide with 2,6-dimethylbenzonitrile gave Compound 53 (yellow solid, 56%). ¹H NMR (300 MHz, CDCl₃) δ: 7.23-7.07 (m, 4H), 7.01 (s, 1H), 6.90 (s, 1H), 5.07 (s, 2H), 4.03 (s, 3H), 4.02 (s, 3H), 2.12 (s, 6H).

6,7-Dimethoxy-3-m-tolylisoquinolin-1-amine (Compound 54)—Reaction of N,N-diethyl-4,5-dimethoxy-2-methylbenzamide with 3-methylbenzonitrile gave Compound 54 (yellow solid, 43%). ¹H NMR (300 MHz, CDCl₃) δ: 8.93 (s, 2H), 7.92 (s, 1H), 7.68-7.64 (m, 2H), 7.37-7.20 (m, 2H), 7.11 (s, 1H), 7.07 (s, 1H), 3.98 (s, 3H), 3.97 (s, 3H), 2.38 (s, 3H).

6,7-Dimethoxy-3-(3,5-dimethoxyphenyl)isoquinolin-1-amine (Compound 55)—Reaction of N,N-diethyl-4,5-dimethoxy-2-methylbenzamide with 3,5-dimethoxybenzonitrile gave Compound 55 (yellow solid, 48%). ¹H NMR (300 MHz, CDCl₃) δ: 7.38 (s, 1H), 7.24 (s, 1H), 7.21 (s, 1H), 7.06 (s, 1H), 7.04 (s, 1H), 6.49 (s, 1H), 5.10 (s, 2H), 4.00 (s, 3H), 3.98 (s, 3H), 3.86 (s, 6H).

6,7-Dimethoxy-3-o-tolylisoquinolin-1-amine (Compound 56)—Reaction of N,N-diethyl-4,5-dimethoxy-2-methylbenzamide with 2-methylbenzonitrile gave Compound 56 (yellow solid, 68%). ¹H NMR (300 MHz, CDCl₃) δ: 7.45-7.03 (m, 7H), 5.01 (s, 2H), 4.02 (s, 3H), 4.02 (s, 3H), 2.40 (s, 3H).

Pharmaceutical Preparation

The following illustrate representative pharmaceutical dosage forms containing the compound of formula (D), or a pharmaceutically acceptable salt thereof (hereafter compound X) for therapeutic or prophylactic use in humans. The formulations may be obtained by conventional procedures well known in the pharmaceutical art and are not limited to the representative pharmaceutical dosage forms.

1) Tablet (Direct Pressure)

The sieved compound X (5.0 mg) is mixed with lactose (14.1 mg), Crosspovidone USNF (0.8 mg) and magnesium stearate (0.1 mg). The mixture is compressed into tablets.

2) Tablet (Hydroassembly)

The sieved compound X (5.0 mg) is mixed with lactose (16.0 mg), starch (4.0 mg) and polysorbate 80 (0.3 mg). Pure water is added to the mixture and the mixture dissolved. The mixture is formed into a particle and the particle dried, sieved and mixed with colloidal silicon dioxide 2.7 mg) and magnesium stearate (2.0 mg). The particle is compressed into tablets.

3) Powder and Capsule

The sieved compound X (5.0 mg) is mixed with lactose (14.8 mg), polyinylpyrrolidone (10.0 mg) and magnesium stearate (0.2 mg). The mixture is filled into No. 5 gelatin capsule using suitable equipment.

4) Injection

Compound X (100 mg), mannitol (180 mg) and Na$_2$HPO$_4$.12H$_2$O (26 mg) are dissolved in about 2974 ml of distilled water.

Biological Tests

1) Growth of Cancer Cell Lines

Cancer cell lines to determine the effect of 5, 6, or 7-substituted-3-(hetero)arylisoquinolinamine compounds were obtained from the following sources: Human MDA-MB-231 (breast), PC3 (prostate), HCT-15 (colon), HCT116 (colon), OVCAR-3 (ovary), Caki-1 (kidney), PANC-1 (pancreas), SNB-19 (glioblastoma) and SK-MEL-28 (melanoma) from the American Type Culture Collection (ATCC) (Manassas, Va.). PC3, OVCAR-3, SK-MEL-28 and SNB-19 were grown in RPMI1640 medium (Invitrogen, Carlsbad, Calif.) supplemented with 10% fetal bovine serum ("FBS"), 1 mM sodium pyruvate, 10 mM HEPES and 100 U/ml penicillin and 100 µg/ml streptomycin ("P/S"). MDA-MB-231, Caki-1, HCT-15 (colon) and PANC-1 cells were maintained in Dulbecco's modified Eagle's medium ("DMEM", Invitrogen) supplemented with 10% FBS, P/S and 10 mM HEPES. HCT116 cells were maintained in DMEM supplemented with 10% FBS, P/S and 10 mM HEPES for in vitro cell proliferation assay and in RPMI1640 medium supplemented with 10% FBS, 1 mM sodium pyruvate, 10 mM HEPES and P/S for in vitro cell cycle analysis. All cells were incubated at 37° C. under humidified 5% CO$_2$.

2) In Vitro Cell Proliferation Assay Against Human Tumor Cell Lines

The growth inhibition of the 5, 6, or 7-substituted-3-(hetero)arylisoquinolinamine derivatives against a variety of human tumor cells was evaluated to study the relative importance of particular substituent groups on the compounds. The 5, 6, or 7-substituted-3-(hetero)arylisoquinolinamine derivatives, prepared as described above, were tested with DMSO as a control.

The growth inhibition assay of representative 5, 6, or 7-substituted-3-(hetero)arylisoquinolinamine derivatives against human tumor cell lines was performed using the Sulforhodamine B ("SRB") method (Skehan et al., J. National Cancer Institute, 82: 1107-1112 (1990)). Briefly, exponentially growing tumor cells were seeded into a 96-well plate at a density of $2-3 \times 10^3$ cells/well and treated with 5, 6, or 7-substituted-3-(hetero)arylisoquinolinamine compounds the next day. Triplicate wells were used for each treatment. The cells were incubated with the various compounds for 96 hours at 37° C. in a humidified 5% CO$_2$ atmosphere. After 96-hour incubation, cells were fixed with 10% trichloroacetic acid ("TCA"), incubated for 1 hour at 4° C., and washed 3 times with tap water. Subsequently, cells were stained with 0.4% sulforhodamine B in 1% acetic acid for 30 minutes, washed 4 times with 1% acetic acid, and air-dried again. After 5 minutes agitation in 10 mM Tris solution, the absorbance of each well was measured at 530 nm using Benchmark Plus Microplate reader (Bio-Rad Laboratories, Hercules, Calif.).

To translate the OD$_{530}$ values into the number of live cells in each well, the OD$_{530}$ values were compared to those on standard OD$_{530}$-versus-cell number curves generated for each cell line. The percent survival was calculated using the formula:

% Survival=live cell number [test]/live cell number [control]×100

The IC$_{50}$ values were calculated by non-linear regression analysis.

Using QSAR and medicinal chemistry techniques, a large number of compounds, including the compounds shown in Table 1-2 above, were synthesized. The synthesized compounds were screened against at least four cancer cell lines, PANC-1, MDA-MB-231, HCT116 and Caki-1, at approximately 1 µM concentration. Compounds showing activity in at least one of these cell lines were selected for further screening. From these compounds, thirty compounds were selected for further evaluation as broad-spectrum anti-proliferative agents as shown in the following Table 3.

TABLE 3

Inhibition of cell growth (IC$_{50}$, µM) by 5, 6, or 7-substituted-3-(hetero)arylisoquinolinamine compounds against human cancer cell lines

| Compound | MDA-MB-231 | PANC-1 | HCT116 | PC3 | OVCAR3 | SK-MEL-28 | Caki-1 | SNB19 |
|---|---|---|---|---|---|---|---|---|
| 10 | 0.11 | 0.17 | 0.14 | 0.26 | 0.071 | 0.14 | 0.15 | 0.19 |
| 11 | 0.34 | 0.65 | 0.45 | 0.77 | 0.27 | 0.46 | 0.47 | 0.63 |
| 13 | 0.021 | 0.019 | 0.017 | 0.019 | 0.014 | 0.032 | 0.022 | 0.032 |
| 14 | 0.021 | 0.018 | 0.023 | 0.024 | 0.016 | 0.032 | 0.023 | 0.028 |
| 15 | 0.15 | 0.19 | 0.18 | 0.23 | 0.14 | 0.33 | 0.17 | 0.25 |
| 16 | 0.027 | 0.026 | 0.029 | 0.048 | 0.025 | 0.045 | 0.038 | 0.057 |
| 21 | 0.059 | 0.11 | 0.064 | 0.19 | 0.071 | 0.11 | 0.068 | 0.094 |
| 23 | 0.15 | 0.24 | 0.19 | 0.24 | 0.15 | 0.35 | 0.12 | 0.26 |
| 24 | 0.44 | 0.93 | 0.67 | >3.0 | 0.49 | 0.80 | 0.35 | 1.13 |
| 25 | 0.14 | 0.31 | 0.19 | 0.25 | 0.18 | 0.34 | 0.13 | 0.29 |
| 26 | 0.93 | 2.27 | 1.36 | 2.98 | 0.79 | 1.80 | 0.75 | 2.23 |
| 27 | 0.66 | 1.75 | 0.85 | 2.69 | 0.57 | 1.41 | 0.51 | 2.15 |
| 28 | 0.13 | 0.22 | 0.16 | 0.19 | 0.16 | 0.22 | 0.11 | 0.23 |
| 30 | 0.18 | 0.38 | 0.24 | 0.43 | 0.18 | 0.41 | 0.16 | 0.47 |
| 31 | 0.15 | 0.24 | 0.17 | 0.25 | 0.17 | 0.29 | 0.12 | 0.28 |
| 33 | 0.55 | 1.59 | 0.70 | 1.84 | 0.57 | 1.07 | 0.46 | 1.51 |
| 34 | 0.14 | 0.21 | 0.17 | 0.24 | 0.16 | 0.23 | 0.12 | 0.24 |
| 35 | 0.57 | 1.28 | 0.59 | 1.19 | 0.47 | 0.72 | 0.69 | 0.75 |
| 36 | 0.15 | 0.20 | 0.18 | 0.22 | 0.15 | 0.25 | 0.16 | 0.21 |
| 37 | 0.32 | 0.68 | 0.47 | 1.01 | 0.51 | 0.67 | 0.22 | 0.78 |
| 38 | 0.17 | 0.47 | 0.21 | 0.42 | 0.24 | 0.41 | 0.14 | 0.48 |
| 41 | 0.72 | 2.14 | 1.22 | 2.76 | 0.91 | 1.62 | 0.59 | 2.20 |
| 42 | 0.079 | 0.18 | 0.12 | 0.20 | 0.13 | 0.21 | 0.065 | 0.20 |

TABLE 3-continued

Inhibition of cell growth (IC$_{50}$, µM) by 5, 6, or 7-substituted-3-(hetero)arylisoquinolinamine compounds against human cancer cell lines

| Compound | MDA-MB-231 | PANC-1 | HCT116 | PC3 | OVCAR3 | SK-MEL-28 | Caki-1 | SNB19 |
|---|---|---|---|---|---|---|---|---|
| 43 | 0.051 | 0.079 | 0.074 | 0.12 | 0.075 | 0.12 | 0.048 | 0.12 |
| 45 | 0.15 | 0.37 | 0.18 | 0.25 | 0.23 | 0.42 | 0.13 | 0.38 |
| 48 | 0.075 | 0.20 | 0.12 | 0.26 | 0.10 | 0.18 | 0.14 | 0.16 |
| 49 | 0.21 | 0.69 | 0.28 | 0.71 | 0.29 | 0.50 | 0.44 | 0.53 |
| 50 | 0.030 | 0.058 | 0.042 | 0.070 | 0.042 | 0.051 | 0.047 | 0.052 |
| 51 | 0.44 | 0.67 | 0.52 | 0.58 | 0.27 | 0.75 | 0.59 | 0.71 |
| 52 | 0.14 | 0.19 | 0.16 | 0.18 | 0.074 | 0.23 | 0.17 | 0.22 |
| 53 | 0.25 | 0.54 | 0.79 | 0.68 | 0.16 | 0.63 | 0.53 | 0.42 |
| 54 | 0.79 | 2.27 | 2.32 | 2.50 | 0.58 | 1.12 | 1.78 | 1.56 |
| 55 | 0.40 | 0.70 | 0.77 | 0.72 | 0.19 | 0.69 | 0.54 | 0.40 |
| 56 | 0.54 | 0.83 | 0.78 | 1.25 | 0.38 | 0.91 | 0.67 | 0.56 |

5, 6, or 7-Substituted-3-(hetero)arylisoquinolinamine derivatives of the invention shown in Table 3 are active against a broad range of tumor cell lines. Many of the compounds have activities, as determined by the IC$_{50}$ value, of significantly less than 1 µM or 0.5 µM or even 0.1 µM. Among compounds in table 3, seventeen compounds such as Compound 10, Compound 13, Compound 14, Compound 15, Compound 16, Compound 21, Compound 25, Compound 28, Compound 31, Compound 34, Compound 36, Compound 42, Compound 43, Compound 45, Compound 48, Compound 50 and Compound 52 showed equal or better activity in growth inhibition of human cancer cell compared to Compound 23,6-methyl-3-(2-methylphenyl)-1-isoquinolinamine claimed in Korea Patent No. 0412319. In particular, Compound 13 and Compound 14 are five to thirteen times more active than compound 23 in tested cell lines. As can be seen from Table 3, many of the other compounds tested exhibited IC$_{50}$<1 µM for a number of cell lines, with IC$_{50}$<0.3 µM in several. Values of IC$_{50}$ of less than or equal to 2.0 µM, 1.5 µM, 1.0 µM or 0.5 µM can reflect significant therapeutic activity. The IC$_{50}$ of the compounds of Table 3 thus reflect significant therapeutic activity.

3) In Vitro Cell Cycle Analysis

This assay was used to determine the ability of 5, 6, or 7-substituted-3-(hetero)arylisoquinolinamine compounds to arrest cells at a specific phase during cell cycle. The day before drug treatment, HCT116 cells were plated at 50-70% saturation in a 10 cm dish in RPMI1640 medium with 10% FBS and then incubated overnight in a humidified 37° C. incubator with 5% CO$_2$. The following day RPMI1640 medium (with 10% FBS) carrying the appropriate concentration of test compound solubilized in DMSO was added to the dishes. No compound control treatment was also included (0.25% DMSO). The cells were then incubated for 12 hours and were harvested by centrifugation at 7,000 rpm for 5 minutes. Cell pellets were resuspended in 0.2 ml of PBS containing 0.1% glucose and 2% FBS. Subsequently, 5 ml ice-cold 70% ethanol was added dropwise with shaking and the treated cells were stored at −20° C. at least 30 minutes. Cells were centrifuged at 2,000 rpm for 5 minutes and washed once with 1 ml PBS with 0.1% glucose and 2% FBS. After removal of the supernatant, cells were resuspended in 0.5 ml of 70 µM propium iodide (PI) solution containing 0.1% Triton X-100, 40 mM sodium citrate, pH 7.4. RNase was added at 50 µg/ml final concentration and cells were incubated at 37° C. for 30 minutes. PI stained cells were analyzed by Guava PCA-AFP instrument using its cell cycle software program (Guava Technologies, Hayward, Calif.) and expressed as percentage of cells in G1, S and G2/M phases of the cell cycle.

The following Table 4 shows percent changes in cell cycle when HCT116 cells were treated with Compound 14 or 43.

TABLE 4

| Treatment | % Cells in G1 | % Cells in S | % Cells in G2/M |
|---|---|---|---|
| DMSO (Control) | 39.4 | 20.5 | 40.1 |
| Compound 14, 0.3 uM | 10.3 | 7.6 | 82.1 |
| Compound 43, 0.3 uM | 15.3 | 10.8 | 73.9 |

4) In Vitro Antitumor Effects Against Paclitaxel-Resistant Hct-15 Human Colorectal Cancer Cells Compound 13 and 14 were tested in colon cancer cells and their antitumor activities were compared with paclitaxel (Taxol®). As shown in Table 5, Compound 13 and 14 showed potent antiproliferative activities in vitro with IC$_{50}$ values in the low nanomolar range in both cells and higher antitumor activities than that of paclitaxel against paclitaxel-resistant HCT-15 colorectal cancer cells. When IC$_{50}$ values were compared in both colon cancer cells, Paclitaxel lost its activity 70 fold in HCT-15 cells but both Compound 13 and 14 showed still strong inhibition of growth of this cells.

TABLE 5

| | Inhibition of cell growth, IC$_{50}$ (µM) | |
|---|---|---|
| Compound | HCT-15 | HCT116 |
| Compound 13 | 0.015 | 0.017 |
| Compound 14 | 0.021 | 0.023 |
| Paclitaxel | 0.14 | 0.0020 |

5) Ex Vivo Xenograft Study

In order to observe the inhibition of growth of tumor in an animal model, an ex vivo xenograft study of nude mice was conducted utilizing Compound 13. Paclitaxel-resistant HCT15 cell suspension (1×10$^6$ cells in 0.2 ml of RPMI) was injected subcutaneously into the right flank of six-week-old female athymic mice (BALB/c nu/nu) on day 0. A sufficient number of mice were injected with HCT15 cell suspension so that tumors in a volume range as narrow as possible were selected for the trial on the day of treatment initiation. Animals with tumors in the proper size range were assigned to various treatment groups. Palcitaxel was used as a positive control. Compound 13 and paclitaxel were dissolved in 5 Cremophor and 5% ethanol in PBS and solvent alone served as vehicle control. All study medications (vehicle control, paclitaxel: 10 mg/kg/day, Compound 13: 10 mg/kg/day) were given by intraperitoneal injections three times per week starting from day 10 and ending on day 29 after inoculation of HCT15 cells. To quantify tumor growth, three perpendicular diameters of the tumors were measured with calipers every 3-5 days, and the body weight of the mice was monitored for toxicity. The tumor volume was calculated using the formula: tumor volume (mm$^3$)=(width)×(length)×(height)×$\pi$/6.

Tumor volume (mean±SEM) in each group of animals is presented in Table 5, which shows a measurement of tumor volume as an indicator of efficacy of Compound 13 against HCT15 human colon carcinoma xenografts. Compound 13 treatment was well tolerated without deaths and no more than 1 g body weight fluctuations was observed. As the result of the measurement of antitumor activity against HCT-15 human colorectal cancer in nude mice at day 29, it was found that Compound 13 has higher antitumor efficacy (69.2% inhibition) than that of the control drug, paclitaxel (48.8% inhibition), as shown in Table 6 below.

TABLE 6

| Treatment | % Inhibition of HCT-15 human colorectal cancer in mice at 29 days |
|---|---|
| Compound 13, 10 mg/kg | 69.2 |
| Paclitaxel, 10 mg/kg | 48.8 |

The novel compounds of the present invention are 5, 6, or 7-substituted-3-(hetero)arylisoquinolinamine derivatives or pharmaceutically acceptable salts thereof which have the strong anti-proliferative effect and are useful for treating hyperproliferative disorders, including cancers, by administering 5, 6, or 7-substituted-3-(hetero)arylisoquinolinamine compounds. The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:
1. A compound according to formula D

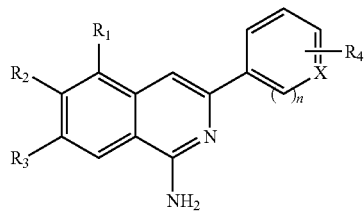

wherein n is 1;
X is C;
either:
(1) $R_2$ is H, halogen, $NH_2$, $NHR_5$, $N(R_5)_2$, —O—$R_5$ or $C_1$-$C_6$ alkyl optionally substituted with —O$R_5$;
$R_1$ is H, halogen, $NH_2$, $NHR_5$, $N(R_5)_2$, and —O—$R_5$;
$R_3$ is H, halogen, $NH_2$, $NHR_5$, $N(R_5)_2$, or $C_1$-$C_6$ alkyl optionally substituted with —O—$R_5$;

$R_4$ is one or two substituents independently selected from 3,4-methylendioxide, halogen, —O—$R_5$ and $C_1$-$C_6$ alkyl optionally substituted with —O—$R_5$; $R_5$ is $C_1$-$C_6$ alkyl; or
(2) $R_1$ is H, $R_2$ and $R_3$ are —O—$CH_3$, and $R_4$ is selected from the group consisting of H, 3-methoxy, 2,6-dimethyl, 3-methyl, 3,5-dimethoxy and 2-methyl; or
(3) $R_1$ and $R_3$ are H, $R_2$ is —O—$CH_3$, and $R_4$ is H; and
when there is more than one group $R_5$, each of the $R_5$ groups may be the same or different or a pharmaceutically acceptable salt thereof;
with the proviso that the compound is not a compound having (a) $R_1$=$R_2$=$R_3$=H or (b) $R_1$=$R_3$=H, $R_2$=methyl, n =1, X =C and $R_4$=H, 2-methyl or 3-methyl.

2. The compound of claim 1 or salt thereof, selected from the group having:
(a) n =1, X =C, $R_1$ =$R_2$ =H, $R_3$ =chloro, and $R_4$ =5-chloro-2-methyl;
(b) n =1, X =C, $R_1$ =$R_3$ =H, $R_2$ =methoxy, and $R_4$ =3,4-dimethoxy;
(c) n =1, X =C, $R_1$ =$R_3$ =H, $R_2$ =methyl, and $R_4$ selected from 4-methyl, 2-methoxy, 3-methoxy, 4-methoxy, 3,4-dimethoxy, 3,4-methylenedioxide, 4-ethoxy, 3,5-dimethoxy, 4methoxy-2-methyl, 3,4,5-trimethoxy, 2-fluoro and 2,6-dimethyl;
(d) n =1, X =C, $R_1$ =$R_2$ =H, $R_3$ =methyl, and $R_4$ selected from 2-methyl, 3-methyl, 2-methoxy, 3-methoxy, 4-methoxy, 4-ethoxy, 2-fluoro, 4-methoxy-2-methyl, 5-methoxy-2- methyl, 2,6-dimethyl, 3,4-dimethoxy, 3,4-methylenedioxide, 3,5-dimethoxy and 3,4,5- trimethoxy;
(e) n =1, X =C, $R_1$ =dimethylamino, $R_2$ =$R_3$ =H, and $R_4$ selected from hydrogen, 2-methyl, 3,4-dimethoxy and 2,6-dimethyl;
(f) n =1, X =C, $R_1$ =$R_3$ =H, $R_2$ =dimethylamino, and $R_4$ =3-methoxy;
(g) n =1, X =C, $R_1$ =H, $R_2$ =$R_3$ =methoxy, and $R_4$ =hydrogen, 2-methyl, 3-methyl, 2,6-dimethyl, 3-methoxy or 3,5-dimethoxy; and
(h) n =1, X =C, $R_1$ =$R_2$ =H, $R_3$ =dimethylamino, and $R_4$ selected from 3-methoxy, 3-methyl, 3,4-dimethoxy and 3,5-dimethoxy.

3. The compound of claim 1 or salt thereof, selected from the group having:
(a) n =1, X =C, $R_1$ =$R_1$=$R_2$ =H, $R_3$ =chloro, and $R_4$ =5-chloro-2-methyl;
(b) n =1, X =C, $R_1$=$R_3$ =H, $R_2$ =methyl, and $R_4$ selected from 4-methyl, 3-methoxy, 4-methoxy-2-methyl, 2,6-dimethyl and 3,4-methylenedioxide;
(c) n =1, X =C, $R_1$ =$R_3$ =H, $R_2$ =dimethylamino, and $R_4$ =3-methoxy;
(d) n =1, X =C, $R_1$ =H, $R_2$ =$R_3$ =methoxy, and $R_4$ =3-methoxy;
(e) n =1, X =C, $R_1$ =$R_2$ =H, $R_3$ =dimethylamino, and $R_4$ selected from 3-methoxy, 3-methyl, 3,4-dimethoxy and 3,5-dimethoxy; and
(f) n =1, X =C, $R_1$ =$R_2$ =H, $R_3$ =methyl, and $R_4$ selected from 2-methyl, 4-methoxy-2-methyl, 5-methoxy-2-methyl, 2,6-dimethyl and 3,4-methylenedioxide.

4. The compound of claim 1 or a salt thereof, selected from the group having:
(a) n =1, X =C, $R_1$ =$R_3$ =H, $R_2$ =dimethylamino, and $R_4$=3-methoxy;

(b) n =1, X =C, R₁ =R₂ =H, R₃ =dimethylamino, and R₄ selected from 3-methoxy, 3-methyl and 3,5-dimethoxy; and (c) n =1, X =C, R₁ =R₂ =H, R₃ =methyl, and R₄ selected from 2-methyl, 4-methoxy-2-methyl, 5-methoxy-2-methyl and 2,6-dimethyl.

5. The compound of claim 1 or salt thereof, having an IC₅₀ of not greater than 0.2 μM with respect to at least one cell line for a tumor selected from breast tumors, prostate tumors, colon tumors, ovary tumors, kidney tumors, pancreas tumors, glioblastoma and melanoma.

6. The compound or salt of claim 5, wherein the cell line is selected from human MDA-MB-231, PC3, HCT116, HCT-15, OVCAR-3, Caki-1, PANC-1, SNB-19 and SK-MEL-28.

7. The compound of claim 1 or salt thereof, having an IC₅₀ of not greater than 0.1 μM with respect to at least one cell line for a tumor selected from breast tumors, prostate tumors, colon tumors, ovary tumors, kidney tumors, pancreas tumors, glioblastoma and melanoma.

8. The compound or salt of claim 7, wherein the cell line is selected from human MDA-MB-231, PC3, HCT116, HCT-15, OVCAR-3, Caki-1, PANC-1, SNB-19 and SK-MEL-28.

9. A pharmaceutical composition comprising a therapeutically effective amount of a compound according to claim 1, or a pharmaceutically acceptable salt thereof, and a pharmaceutically acceptable carrier or diluent.

10. A method for treating a hyperproliferative disorder comprising administering a composition comprising a compound according to formula D

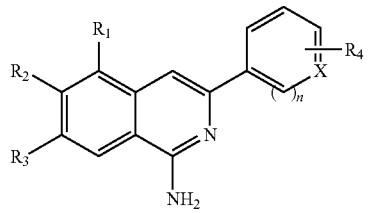

D wherein n is 1;
X is C;
either:
(1) R₂ and R₃ are independently H, halogen, NH₂, NHR₅, N(R₅)₂, —O—R₅ or C₁-C₆ alkyl optionally substituted with —O—R₅;
R₁ is H, halogen, NH₂, NHR₅, N(R₅)₂, and —O—R₅;
R₄ is one or two substituents independently selected from 3,4-methylendioxide, halogen, —O—R₅ and C₁-C₆ alkyl optionally substituted with —O—R₅;
R₅ is C₁-C₆ alkyl; or
(2) R₁ is H, R₂ and R₃ are —O—CH₃, and R₄ is H;
(3) R₁ and R₃ are H, R₂ is —O—CH₃, and R₄ is H; and
when there is more than one group R₅, each of the R₅ groups may be the same or different or a pharmaceutically acceptable salt thereof;
with the proviso that the compound is not a compound having (a) R₁ =R₂ =R₃ =H or (b) R₁ =R₃ =H, R₂ =methyl, n =1, X =C and R₄ =H, 2-methyl or 3-methyl.

11. The method of claim 10, wherein the compound or salt thereof is selected from the group having:

(a) n =1, X =C, R₁ =R₂ =H, R₃ =chloro, and R₄ =5-chloro-2-methyl;
(b) n =1, X =C, R₁ =R₃ =H, R₂ =methoxy, and R₄ =3,4-dimethoxy;
(c) n =1, X =C, R₁=R₃ =H, R₂ =methyl, and R₄ selected from 4-methyl, 2-methoxy, 3-methoxy, 4-methoxy, 3,4-dimethoxy, 3,4-methylenedioxide, 4-ethoxy, 3,5-dimethoxy, 4-methoxy-2-methyl, 3,4,5-trimethoxy, 2-fluoro and 2,6-dimethyl;
(d) n =1, X =C, R₁ =R₂ =H, R₃ =methyl, and R₄ selected from 2-methyl, 3-methyl, 2-methoxy, 3-methoxy, 4-methoxy, 4-ethoxy, 2-fluoro, 4-methoxy-2-methyl, 5-methoxy-2-methyl, 2,6-dimethyl, 3,4-dimethoxy, 3,4-methylenedioxide, 3,5-dimethoxy and 3,4,5-trimethoxy;
(e) n =1, X =C, R₁ =dimethylamino, R₂ =R₃ =H, and R₄ selected from hydrogen, 2-methyl, 3,4-dimethoxy and 2,6-dimethyl;
(f) n =1, X =C, R₁ =R₃ =H, R₂ =dimethylamino, and R₄ =3-methoxy;
(g) n =1, X =C, R₁ =H, R₂ =R₃ =methoxy, and R₄ =hydrogen, 2-methyl, 3-methyl, 2,6-dimethyl, 3-methoxy or 3,5-dimethoxy; and
(h) n =1, X =C, R₁ =R₂ =H, R₃ =dimethylamino, and R₄ selected from 3-methoxy, 3-methyl, 3,4-dimethoxy and 3,5-dimethoxy.

12. The method of claim 10, wherein the compound or salt thereof is selected from the group having:
(a) n =1, X =C, R₁ =R₁ =R₂ =H, R₃ =chloro, and R₄ =5-chloro-2-methyl;
(b) n =1, X =C, R₁ =R₃ =H, R₂ =methyl, and R₄ selected from 4-methyl, 3-methoxy, 4-methoxy-2-methyl, 2,6-dimethyl and 3,4-methylenedioxide;
(c) n =1, X =C, R₁ =R₃ =H, R₂ =dimethylamino, and R₄ =3-methoxy;
(d) n =1, X =C, R₁ =H, R₂ =R₃ =methoxy, and R₄ =3-methoxy;
(e) n =1, X =C, R₁ =R₂ =H, R₃ =dimethylamino, and R₄ selected from 3-methoxy, 3-methyl, 3,4-dimethoxy and 3,5-dimethoxy; and
(f) n =1, X =C, R₁ =R₂ =H, R₃ =methyl, and R₄ selected from 2-methyl, 4-methoxy-2-methyl, 5-methoxy-2-methyl, 2,6-dimethyl and 3,4-methylenedioxide.

13. The method of claim 10, wherein the compound or salt thereof is selected from the group having:
(a) n =1, X =C, R₁ =R₃ =H, R₂ =dimethylamino, and R₄ =3-methoxy;
(b) n =1, X =C, R₁ =R₂ =H, R₃ =dimethylamino, and R₄ selected from 3-methoxy, 3-methyl and 3,5-dimethoxy; and
(c) n =1, X =C, R₁ =R₂ =H, R₃ =methyl, and R₄ selected from 2-methyl, 4-methoxy-2-methyl, 5-methoxy-2-methyl and 2,6-dimethyl.

14. The method of claim 10, wherein said hyperproliferative disorder is a tumor.

15. The method of claim 14, wherein the tumor is selected from breast tumors, prostate tumors, colon tumors, ovary tumors, kidney tumors, pancreas tumors, glioblastoma and melanoma.

16. The method of claim 10, wherein the compound or salt thereof is conjugated to a targeting moiety, optionally through a linking agent.

* * * * *